(12) United States Patent
Thirumalai Rajan et al.

(10) Patent No.: US 10,351,556 B2
(45) Date of Patent: Jul. 16, 2019

(54) PROCESS FOR THE PREPARATION OF 1,3-THIAZOL-5-YLMETHYL [(2R,5R)-5-{[(2S)-2-[(METHYL{[2-(PROPAN-2-YL)-1,3-THIAZOL-4YL] METHYL} CARBAMOYL) AMINO]-4-(MORPHOLIN-4-YL) BUTANOYL]AMINO)-1,6-DIPHENYLHEXAN-2-YL]CARBAMATE

(71) Applicants: MSN LABORATORIES PRIVATE LIMITED, Hyderabad, Telangana (IN); Srinivasan Thirumalai Rajan, Hyderabad, Telangana (IN); Sajja Eswaraiah, Hyderabad, Telangana (IN); Gutta Madhusudhan, Hyderabad, Telangana (IN); Komati Satyanarayana, Hyderabad, Telangana (IN); Jakku Malleswara Reddy, Hyderabad, Telangana (IN)

(72) Inventors: Srinivasan Thirumalai Rajan, Telangana (IN); Sajja Eswaraiah, Telangana (IN); Gutta Madhusudhan, Telangana (IN); Komati Satyanarayana, Telangana (IN); Jakku Malleswara Reddy, Telangana (IN)

(73) Assignee: MSN LABORATORIES PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 15/551,856

(22) PCT Filed: Feb. 17, 2016

(86) PCT No.: PCT/IN2016/000043
§ 371 (c)(1),
(2) Date: Dec. 22, 2017

(87) PCT Pub. No.: WO2016/132378
PCT Pub. Date: Aug. 25, 2016

(65) Prior Publication Data
US 2018/0030043 A1    Feb. 1, 2018

(30) Foreign Application Priority Data

Feb. 18, 2015 (IN) .............. 778/CHE/2015
Feb. 20, 2015 (IN) .............. 815/CHE/2015

(51) Int. Cl.
| | | |
|---|---|---|
| C07D 417/12 | (2006.01) | |
| C07D 277/28 | (2006.01) | |
| A61K 9/16 | (2006.01) | |
| A61K 31/5377 | (2006.01) | |
| C07C 269/04 | (2006.01) | |
| C07C 271/20 | (2006.01) | |

(52) U.S. Cl.
CPC .......... *C07D 417/12* (2013.01); *A61K 9/1611* (2013.01); *A61K 9/1652* (2013.01); *A61K 9/1682* (2013.01); *A61K 31/5377* (2013.01); *C07C 269/04* (2013.01); *C07C 271/20* (2013.01); *C07D 277/28* (2013.01)

(58) Field of Classification Search
CPC .................................................. C07D 417/12
See application file for complete search history.

(56) References Cited

U.S. PATENT DOCUMENTS

| | | | |
|---|---|---|---|
| 8,853,210 B2 * | 10/2014 | Polniaszek ............ | C07C 209/62 514/236.8 |
| 2014/0088304 A1 | 3/2014 | Polliniaszek et al. | |

FOREIGN PATENT DOCUMENTS

| | | |
|---|---|---|
| WO | WO 2012/151165 | 11/2012 |
| WO | WO 2014/105777 | 7/2014 |

OTHER PUBLICATIONS

Written Opinion of the International Searching Authority issued in International Patent Application No. PCT/IN2016/000043, dated Aug. 1, 2016.
International Search Report issued in International Patent Application No. PCT/IN2016/000043, dated Aug. 1, 2016.

* cited by examiner

*Primary Examiner* — Golam M Shameem
(74) *Attorney, Agent, or Firm* — IP Pundit LLC

(57) ABSTRACT

The present invention relates to novel processes for the preparation 1,3-Thiazol-5-ylmethyl[(2R,5R)-5-{[(2S)-2-[(methyl{[2-(propan-2-yl)-1,3-thiazol-4-yl]methyl} carbamoyl)amino]-4-(morpholin-4-yl)butanoyl]amino}-1,6-diphenylhexan-2-yl] carbamate having the following structural formula-1 and it's intermediates thereof.

Formula-1

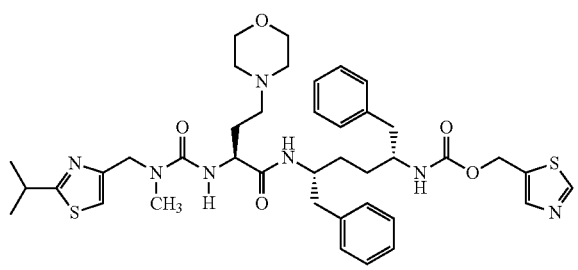

16 Claims, 3 Drawing Sheets

DSC

PROCESS FOR THE PREPARATION OF 1,3-THIAZOL-5-YLMETHYL [(2R,5R)-5-{[(2S)-2-[(METHYL{[2-(PROPAN-2-YL)-1,3-THIAZOL-4YL] METHYL} CARBAMOYL) AMINO]-4-(MORPHOLIN-4-YL)BUTANOYL] AMINO)-1,6-DIPHENYLHEXAN-2-YL] CARBAMATE

RELATED APPLICATIONS

This application is a national phase application under 35 U.S.C. § 371 of International Application No. PCT/IN2016/000043, filed on Feb. 17, 2016, which claims priority to Indian patent application number 778/CHE/2015 filed on Feb. 18, 2015 and 815/CHE/2015 filed on Feb. 20, 2015; the disclosure of which is incorporated herein by reference in its entirety.

FIELD OF THE INVENTION

The present invention provides novel processes for the preparation of 1,3-Thiazol-5-ylmethyl[(2R,5R)-5-{[(2S)-2-[(methyl{[2-(propan-2-yl)-1,3-thiazol-4-yl] methyl}carbamoyl) amino]-4-(morpholin-4-yl)butanoyl] amino}-1,6-diphenylhexan-2-yl]carbamate having the following structural formula-1

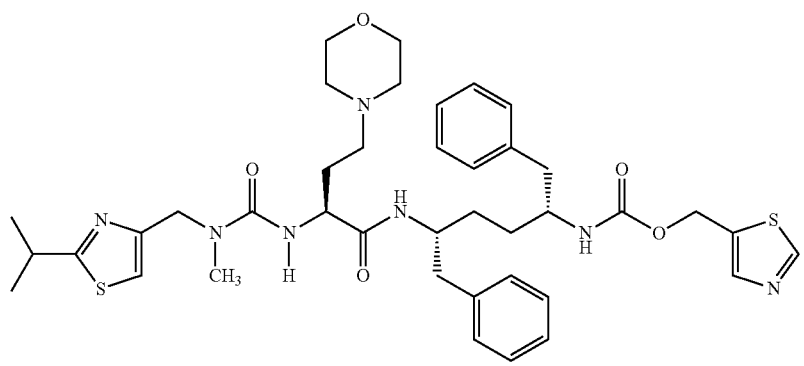

The present invention also provides novel intermediates which are useful in the preparation of the compound of formula-1.

Further, the present invention also provides the solid dispersion of 1,3-Thiazol-5-ylmethyl[(2R,5R)-5-{[(2S)-2-[(methyl {[2-(propan-2-yl)-1,3-thiazol-4-yl] methyl}carbamoyl) amino]-4-(morpholin-4-yl)butanoyl] amino}-1,6-diphenylhexan-2-yl]carbamate combination with one or more pharmaceutically acceptable carrier.

BACKGROUND OF THE INVENTION 1,3-Thiazol-5-ylmethyl [(2R,5R)-5-{[(2S)-2-[(methyl{ [2-(propan-2-yl)-1,3-thiazol-4-yl]methyl}carbamoyl) amino]-4-(morpholin-4-yl) butanoyl]amino}-1,6-diphenylhexan-2-yl]carbamate having the structural formula-1 is Cytochrome P450 monooxygenase inhibitors and also known as Cobicistat. The compound of formula-1 of the present invention is used in the treatment of human immunodeficiency virus (HIV). Cobicistat is a component of a four-drug, fixed-dose combination for HIV treatment Elvitegravir/Cobicistat/Emtricitabine/Tenofovir (known as the "Quad Pill" or Stribild®). The Quad Pill/Stribild was approved by the FDA in August 2012 for use in the United States. This is also approved in US under the brand name of TYBOST®.

Cobicistat is a potent inhibitor of cytochrome P450 3A enzymes, including the important CYP3A4 subtype. It also inhibits intestinal transport proteins, increasing the overall absorption of several HIV medications, including atazanavir, darunavir, and tenofovir alafenamide fumarate.

Various synthetic routes are available for the synthesis of the compound of formula-1. U.S. Pat. No. 8,148,374 first disclosed the compound of formula-1 and process for its preparation. The compound of formula-1 is a straight chain having three peptide bonds. US '374 disclose some possibilities to preparation of the compound of formula-1.

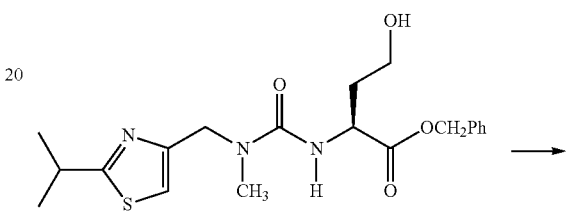

Formula-1

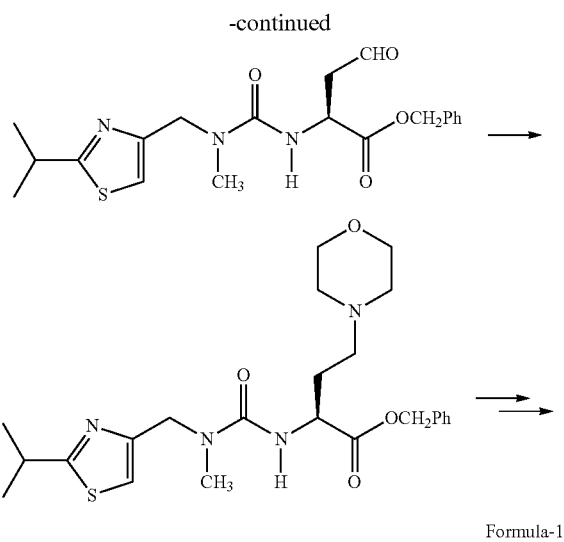

Formula-1

The disclosed process involves the usage of strong basic agents leading to lower yields and less purity due to the formation of byproducts.

Cobicistat (Tybost, and component of Stribild, Gilead) is a novel cytochrome P450 (CYP) enzyme (CYP3A4) inhibitor used as a "booster" in combination with some HIV treatments, e.g. protease inhibitors, to reduce their metabolism during absorption and so increase the amount of unchanged drug reaching the systemic circulation. Ritonavir is also used as such a boosting agent but cobicistat differs in that it has no anti-viral activity of its own and is purely used to modify pharmacokinetics.

Cobicistat drug substance does not occur in crystalline form and is isolated as amorphous, hygroscopic solid foam of low glass transition temperature which readily transforms under ambient conditions via a moisture and temperature-driven phase transformation into a rubber-like material that is difficult to process into dosage forms. The removal of the absorbed moisture and reversion to the original solid form does not occur.

International patent publication number WO 2009/135179 A1 discusses the difficulties associated with processing the compound of formula-1 and describes combining the compound of formula-1 with solid carrier particles such as silicon-dioxide to improve the physical properties of the resulting solid material. But the silicon-dioxide carrier particles contribute to the overall weight and volume of the solid so that significantly more material is required in a formulation to achieve a given dose of the compound of formula-1. Accordingly, there is a need for solid forms of the compound of formula-1 that have the beneficial properties of the solids described in WO2009/135179 A1 but lack the inert carrier particles that contribute to the weight and the volume of the solid.

By adsorbing onto silica by evaporation from dichloromethane solution of drug as part of the isolation of the cobicistat, a free flowing powder is produced.

The finished dosage form using the adsorbate showed bio-equivalence for cobicistat with dosage forms prepared by the ethanol/water high shear granulation process. For cobicistat, formulation technology has dealt with challenging physical properties of an active pharmaceutical ingredient and provided an approach to improved handling and manufacturing of dosage forms.

Several methods to improve the dissolution characteristics of compounds have been reported, including particle size reduction, formation of solvates, complexes and micro spheres. Additionally, attempts have been made to improve bio-availability provided by solid dosage forms by forming solid dispersions of drugs. Solid dispersions create a mixture of a poorly water soluble drug and highly soluble carriers. Solid dispersions may increase bio-availability by decreasing the energy required for solubilizing the drug and increasing the stability of the drug in solution. Traditionally these methods carry inherent limitations concerning physical stabilities of the solid dispersion on storage, problems with grinding or difficulty of removal of the solvent. Furthermore, it is important that the drug released from the solid phase does not precipitate in the small intestine tract but remains water-soluble in the aqueous fluids of the small intestine tract, since such precipitation results in low bio-availability.

The present invention provides solid dispersions having more stability and greater bioequivalence.

The present inventors have developed a novel processes for the preparation of the compound of formula-1 it has many advantages; like using simple and mild bases such as alkali metal salts avoiding pyrophoric bases making it conducive for large scale production at an industrial level; Lesser reaction times; Avoiding column chromatography technique for the purification. It also avoids the formation by-products and unwanted isomers especially in the final product, improving the yield and quality. Formation of N-oxide impurity is inhibiting by the usage of antioxidant in the reaction.

BRIEF DESCRIPTION OF THE INVENTION

The first aspect of the present invention is to provide a novel process for the preparation of the compound of formula-1.

The second aspect of the present invention is to provide an improved process for the preparation of the compound of formula-13.

The third aspect of the present invention is to provide a novel intermediate compound of the general formula-8 or its salts.

The fourth aspect of the present invention is to provide a process for the preparation of compound of the general formula-8 or its salts.

The fifth aspect of the present invention is to provide a solid dispersion of 1,3-thiazol-5-ylmethyl[(2R,5R)-5-{[(2S) 2-[(methyl{[2-(propan-2-yl)-1,3-thiazol-4-yl]methyl} carbamoyl) amino]-4-(morpholin-4yl)butanoyl]amino}-1,6-diphenylhexan-2-yl]carbamate compound of formula-1 with one or more pharmaceutically acceptable carrier.

The sixth aspect of the present invention is to provide a solid dispersion of the compound of formula-1 in combination with cellulose derivatives.

The seventh aspect of the present invention is to provide a process for the preparation of a solid dispersion of 1,3-thiazol-5-ylmethyl[(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenyl hexan-2-yl]carbamate compound of formula-1 in combination with one or more pharmaceutically acceptable carrier.

The eighth aspect of the present invention is to provide a novel process for the preparation of solid dispersion of compound of formula-1 with silicondioxide.

DETAILED DESCRIPTION OF THE INVENTION

Figure 1:
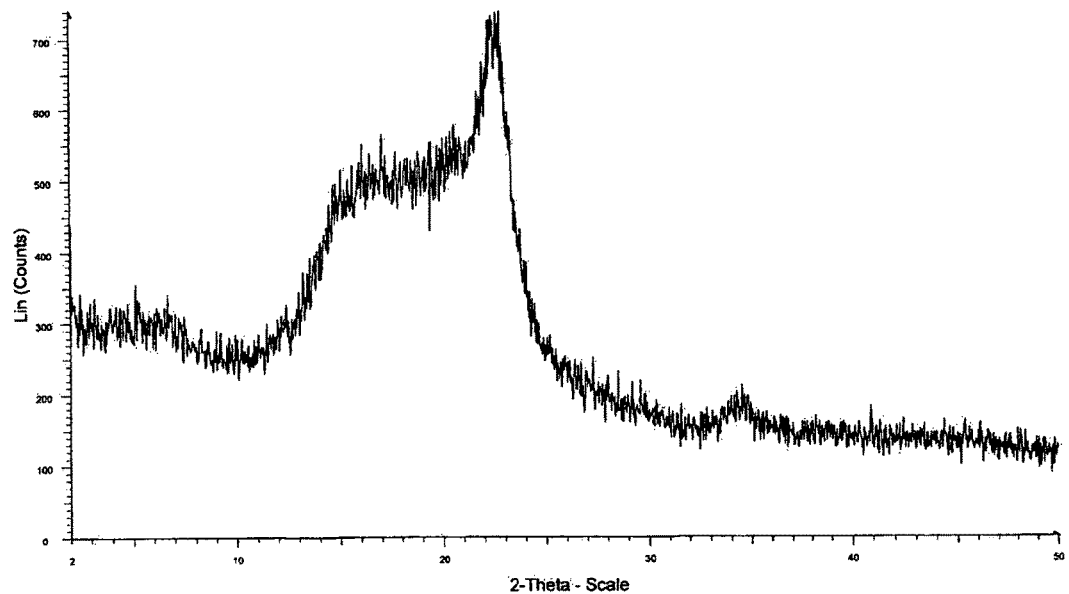
FIG. 1: Illustrates the PXRD pattern of solid dispersion of the compound of formula-1 with MCC in the ratio of 1:1.

The present invention provides a solid dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenylhexan-2-yl]carbamate and process for its preparation thereof.

A conventional method for the manufacture of a solid dispersion relates to a fusion process which is characterized by melting a drug substance and a pharmaceutical acceptable carrier together at elevated temperature and, then, cooling the melt to solidify. Another conventional method for the manufacture of a solid dispersion relates to a solvent process which is characterized by dissolving a drug substance and a pharmaceutical acceptable carrier in an appropriate solvent and, then, removing the solvent. Additional method for the manufacture of a solid dispersion relates to mixing a drug substance and a pharmaceutical acceptable carrier through milling.

As used herein the term a "solid dispersion" is a drug-containing pharmaceutical bulk substance in which the drug is dispersed in a pharmaceutical acceptable carrier such as a polymer, cellulose derivative, a co-polymer, or a mixture thereof.

As used herein the term "pharmaceutically acceptable carrier" as used herein, refers to both polymeric and non-polymeric carriers; hydrophilic and hydrophobic carriers; cellulose derivatives; polyvinylpyrrolidone (PVP), copovidone and silicondioxide.

The term "stable amorphous cobicistat" refers to solid dispersion of cobicistat with silicondioxide or solid dispersion of cobicistat with pharmaceutically acceptable carrier.

As used herein the term suitable cellulose derivatives used in the present invention refers to cellulose acetate, cellulose nitrate, cellulose xanthate, carboxy methyl cellulose, micro crystalline cellulose herein referred as "MCC", methyl cellulose, ethyl cellulose, hydroxypropylcellulose (HPC), hydroxypropylmethylcellulose (HPMC) and hydroxy ethyl cellulose and polymers such as suitable water soluble polymer is a chemically modified cellulose and/or cellulose ether, and in particular is selected from the group consisting of alkylcellulose, e.g. methylcellulose, ethylcellulose, propylcellulose; hydroxalkylcellulose, e.g. hydroxy methylcellulose, hydroxyethyl cellulose, hydroxypropylcellulose; hydroxyalkyl alkylcellulose, e.g. hydroxyethyl methylcellulose (HEMC), hydroxypropylmethylcellulose (HPMC); carboxyalkylcellulose, e.g carboxymethylcellulose (CMC), carboxymethyl hydroxyethylcellulose (CMHEC), hydroxyethylcarboxy methylcellulose (HECMC), sodium carboxymethylcellulose, cellulose acetate phthalate (CAP), hydroxypropylmethylcellulose acetate (HPMCA), hydroxypropylmethylcellulose phthalate (HPMCP), hydroxypropyl methylcellulose acetate succinate (HPMC-AS) or mixtures thereof.

The term "suitable solvent" used in the present invention refers to "hydrocarbon solvents" such as n-pentane, n-hexane, n-heptane, cyclohexane, methyl cyclohexane, cycloheptane, pet ether, toluene, xylene and the like; "ether solvents" such as dimethyl ether, diethyl ether, diisopropyl ether, methyl tert-butyl ether, ethyl tert-butyl ether, di-tert-butyl ether, dimethoxy methane, 1,2-dimethoxyethane, diglyme, 1,4-dioxane, tetrahydrofuran, 2-methyl tetrahydrofuran and the like; "ester solvents" such as methyl acetate, ethyl acetate, n-propyl acetate, isopropyl acetate, n-butyl acetate, iso-butyl acetate, tert-butyl acetate, diethyl carbonate and the like; "polar-aprotic solvents" such as dimethylacetamide (DMAc), N,N-dimethylformamide (DMF), dimethylsulfoxide (DMSO), N-methyl-2-pyrrolidone (NMP), hexamethylphosphoramide (HMPA) and the like; "nitrite solvents" such as acetonitrile, propionitrile, butyronitrile, isobutyronitrile and like; "chloro solvents" such as dichloromethane, dichloroethane, chloroform, carbon tetrachloride and the like; "ketone solvents" such as acetone, methyl ethyl ketone, diethyl ketone, methyl isopropyl ketone, methyl isobutyl ketone and the like; "alcohol solvents" such as methanol, ethanol, n-propanol, isopropanol, n-butanol, iso-butanol, tert-butanol, 2-pentanol, ethylene glycol, diethylene glycol, propylene glycol, 2-ethyl hexanol, benzyl alcohol and the like; "polar solvents" such as water; acetic acid or mixtures thereof.

The term "suitable base" used in the present invention refers to inorganic bases selected from "alkali metal carbonates" such as sodium carbonate, potassium carbonate, lithium carbonate, cesium carbonate and the like; "alkali metal bicarbonates" such as sodium bicarbonate, potassium bicarbonate, lithium bicarbonate, cesium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide and the like; "alkali metal amides" such as sodium amide, potassium amide, lithium amide, lithium diisopropyl amide (LDA), sodium bis(trimethylsilyl)amide (NaHMDS), potassium bis(trimethylsilyl)amide, lithium bis(trimethysilyl)amide (LiHMDS) and the like; "alkyl metals" such as n-butyl lithium and like; "metal hydrides" such as lithium hydride, sodium hydride, potassium hydride and the like; "alkali metal phosphates" such as disodium hydrogen phosphate; dipotassiumhydrogen phosphate; and "organic bases" selected from but not limited to methyl amine, ethyl amine, diisopropyl amine, diisopropylethyl amine (DIPEA), diisobutylamine, triethylamine, tert.butyl amine, pyridine, 4-dimethylaminopyridine (DMAP), N-methyl morpholine (NMM), n-methyl pyridine (NMP), 1,8-diazabicyclo[5.4.0]undec-7-ene (DBU), 1,5-diazabicyclo[4.3.0]non-5-ene (DBN), 1,4-diazabicyclo[2.2.2]octane (DABCO), imidazole; or mixtures thereof.

The term "acid" used in the present invention refers to inorganic acids selected from hydrochloric acid, hydrobromic acid, sulfuric acid, nitric acid, phosphoric acid etc; organic acids such as acetic acid, maleic acid, malic acid, tartaric acid, oxalic acid, trifluoroacetic acid, methane sulfonic acid, p-toluene sulfonic acid; chiral acids such as S-(+) mandelic acid, R-(−) mandelic acid, L-(+)tartaric acid, D-(−) tartaric acid, L-malic acid, D-malic acid, D-maleic acid, (−) -naproxen, (+)-naproxen, (1R)-(−)-camphor sulfonic acid, (IS)-(+)-camphor sulfonic acid, (1R) -(+)-bromocamphor-10-sulfonic acid, (1S)-(−)-bromocamphor-10-sulfonic acid, (−)-Dibenzoyl-L-tartaric acid, (−)-Dibenzoyl-L-tartaricacid monohydrate, (+)-Dibenzoyl-D-tartaric acid, (+) -Dibenzoyl-D-tartaric-acid monohydrate, (+)-diparatolyl-D-tataric acid, (−)-dipara-tolyl-L-tataric acid, L(−)-pyroglutamic acid, L(+)-pyroglutamic acid, (−)-lactic acid, L-lysine, D-lysine etc., and like.

The term "salts" used in the present invention refers to acid addition salts selected from inorganic acids such as hydrochloric acid, hydrobromic acid, sulfuric acid, nitric acid, phosphoric acid; organic acids such as acetic acid, maleic acid, malic acid, oxalic acid, trifluoroacetic acid, methane sulfonic acid, p-toluene sulfonic acid; chiral acids such as S-(+) mandelic acid, R-(−) mandelic acid, L-(+) tartaric acid, D-(−)tartaric acid, L-malic acid, D-malic acid, D-maleic acid, (−)-naproxen, (+)-naproxen, (1R)-(−)-camphor sulfonic acid, (IS)-(+)-camphor sulfonic acid (1R)-(+)-bromocamphor-10-sulfonic acid, (1S)-(−)-bromocamphor-10-sulfonic acid, (−)-Dibenzoyl-L-tartaric acid, (−)-Dibenzoyl-L-tartaricacid monohydrate, (+) -Dibenzoyl-D-tartaric acid, (+)-Dibenzoyl-D-tartaric acid monohydrate, (+)-dipara-tolyl-D-tataric acid, (−)-dipara-tolyl-L-tataricacid, L(−)-pyroglutamic acid, L(+)-pyroglutamic acid, (−)-lactic acid, L-lysine, D-lysine etc., and like.

The term "oxidizing agent" used in the present invention includes, for example, peracids such as m-chloroperbenzoic acid, peracetic acid, and the like; and an inorganic oxidizing agent such as manganese dioxide, sodium periodate, hydrogen peroxide, dinitrogen tetroxide, hydroperoxide, iodobenzene acetate, t-butyl hypochlorite, sulfuryl chloride, potassium peroxymonosulfate, sodium hypochlorite in presence of TEMPO, DABCO, Dess-martin reagent, oxaloyl chloride in DMSO etc.

The term "acid catalyst" used in the present invention refers to acids selected from conc.hydrochloric acid, conc..sulfuric acid or thionylchloride; trimethylsilyl diazomethane (only for methyl ester) etc., and the like.

The term "halogenating agent" used in the present invention refers to brominating agent such as N-bromosuccinamide (NBS), bromine, carbon tetrabromide, phosphorous bromide, phosphorous tribromide, phosphorous pentabromide or sodium bromide in combination with trimethylsilyl chloride; the term chlorinating agent is selected from thionyl chloride, oxalyl chloride, sulfuryl chloride, phosphorous oxychloride, carbon tetra chloride, phosphorous trichloride, phosphorous pentachloride, N-chlorosuccinamide (NCS) and like; and iodinating agent such as trimethyl iodide, hydrogen iodide or sodium iodide optionally in combination with triphenyl phosphine, trimethylsilyl chloride.

The term "condensing agent or coupling agent" used in the present invention is selected form N,N'-dicyclohexylcarbodiimide (DCC), N,N'-diisopropylcarbodiimide (DIC), carbonyldiimidazole (CDI), 1-ethyl-3-(3-dimethylaminopropyl)carbodiimide hydrochloride (EDC.HCl), O-(7-azabenzotriazole-1-yl)-N,N,N',N'-tetramethyl uronium hexafluoro phosphate (HATU), alkyl or aryl chloroformates such as ethyl chloroformate, benzylchloroformate, diphenylphosphoroazidate (DPPA), thionyl chloride, pivalyl chloride, oxalyl chloride, phosphorous oxychloride, phosphorous pentachloride, 4-methyl-2-oxopentanoyl chloride (i-BuCOCOCl), benzotriazol-1-yl-oxytripyrrolidino phosphonium hexafluorophosphate (PyBOP), methane sulfonyl chloride and the like; optionally in combination with 1-hydroxy-7-azatriazole (HOAt), 1-hydroxybenzotriazole (HOBt), 1-hydroxy-1H-1,2,3-triazole-4-carboxylate (HOCt), O-(benzotriazol-1-yl)-N,N,N',N'-tetramethyluronium tetrafluoroborate (TBTU), N-hydroxysuccinamide (HOSu), N-hydroxysulfosuccinimide (Sulfo-NHS), 4-dimethylaminopyridine (DMAP).

The term "amine protecting group (or)N-protecting group" used in the present invention is selected from but not limited to tert-butyloxycarbonyl (BOC), benzyloxycarbonyl (Cbz), 9-fluorenylmethyloxy carbonyl (FMOC), acetyl (Ac), benzoyl (Bz), benzyl (Bn), carbamate group, p-methoxyphenyl (PMP), p-methoxybenzyl (PMB), 3,4-dimethoxy benzyl (DMPM), tosyl (Ts), trifluoroacetyl (TFA) group and the like.

The suitable amine protecting agent is selected such that it is capable of protecting the nitrogen atom with any of the above mentioned amine protecting groups.

Suitable amine protecting agent is selected from but not limited to di-tert.butyl dicarbonate (DIBOC), benzyl chloroformate, fluorenylmethyloxy carbonyl chloride (FMOC chloride), acetyl chloride, acetic anhydride, benzoyl halides, benzyl halides, tosyl halides, tosyl anhydrides, alkyl trifluoroacetates such as methyl trifluoroacetate, ethyl trifluoroacetate, isopropyl trifluoroacetate, vinyl trifluoroacetate, trifluoroacetic acid, trifluoroacetyl chloride and the like.

The term "deprotecting agent" used in the present invention is selected based on the protecting group employed. The deprotecting agent is selected from but not limited to acids such as hydrochloric acid, hydrobromic acid, sulfuric acid, nitric acid, aq.phosphoric acid, trifluoroacetic acid, methane sulfonic acid, p-toluene sulfonic acid; acetyl chloride in combination with alcohols; bases such as alkali metal hydroxides, alkali metal carbonates, cesium carbonate/imidazole, alkali metal bicarbonates, ammonia, ammonium cerium(IV) nitrate (CAN); and organic bases such as methylamine, ethylamine, diethylamine, triethylamine, piperidine; hydrogenating agents such as Pd/C, Pd(OH)$_2$/C (Pearlman's catalyst), palladium acetate, platinum oxide, platinum black, sodium borohydride, Na-liquid ammonia, Raney-Ni, tri($C_1$-$C_6$)alkylsilanes, tri($C_1$-$C_6$)alkylsilyl halides and the like.

The term "reducing agent" used in the present invention refers to palladium catalyst, such as selected from: palladium on carbon, palladium on alumina, palladium on barium sulfate, palladium on calcium carbonate, palladium on barium carbonate, palladium on strontium carbonate, palladium on silica, and palladium hydroxide on carbon (Pearlman's catalyst), Pt/C, PtO$_2$, Fe, Fe in acidic media like acetic acid, NH4Cl; Sn—HCl, Stannous chloride (SnCl$_2$), Zn in acidic media like acetic acid, NH$_4$Cl, Zinc dust, Ni, Raney Ni, Lithium aluminium hydride, sodium borohydride, potassium borohydride, lithium borohydride, sodium aluminium hydride. Optionally, the product is contacted with a strong inorganic or organic acid prior to conducting the hydrogenation. The acid is selected from hydrochloric, hydrobromic acid, sulfuric acid, phosphoric acid, formic acid, acetic acid, trifluoroacetic acid, trichloroacetic acid, oxalic acid, tartaric acid, citric acid, malic acid, benzoic acid, 4-nitrobenzoic acid, methanesulfonic acid, trifluoromethane sulfonic acid, benzenesulfonic acid, 4-chlorobenzenesulfonic acid and 4-toluenesulfonic acid.

The term "antioxidant" used in the present invention is used to inhibit the formation of N-oxide impurity and is selected from thiols, ascorbic acid; preferably L-ascorbic acid.

The first aspect of the present invention provides a novel process for the preparation of 1,3-Thiazol-5-ylmethyl[(2R, 5R)-5-{[(2S)-2-[(methyl [2-(propan-2-yl)-1,3-thiazol-4-yl] methyl}carbamoyl)amino]-4-(morpholin-4-yl)butanoyl] amino}-1,6-diphenylhexan-2-yl]carbamate compound of formula-1 comprising of:

a) Reacting L-methionine with bromoacetic acid in presence of a suitable acid in a suitable solvent to provide (S)-3-aminodihydrofuran-2(3H)-one compound of formula-3 or its salts,
b) reacting the compound of formula-3 or its salts with the 1-(2-isopropylthiazol-4-yl)-N-methylmethanamine compound of formula-2 or its salts in presence of a suitable coupling agent in a suitable solvent to provide (S)-1-((2-isopropylthiazol-4-yl)methyl)-1-methyl-3-(2-oxotetrahydrofuran-3-yl)urea compound of formula-4,
c) treating the compound of formula-4 with a suitable halogenating agent in the suitable alcohol solvent and optionally in a mixture of solvent followed by reacting the obtained compound with morpholine to provide a corresponding ester compound of general formula-5,
d) optionally converting the compound of general formula-5 into its acid addition salts of compound of general formula-6,
e) reacting the compound of general formula-5 or formula-6 with a suitable base in a suitable solvent to provide compound of general formula-7,
which on in-situ reacting with the compound of general formula-8 or its salts in presence of a suitable coupling agent in a suitable solvent to provide the compound of general formula-9
which on in-situ treating with a suitable deprotecting agent in a suitable solvent to provide compound of formula-10,
f) optionally converting the compound of formula-10 into its acid addition salts to provide the compound of general formula-11,
g) optionally treating the compound of general formula-11 with a suitable base in a suitable solvent to provide compound of formula-10,
h) reacting the compound of formula-10 with the compound of general formula-13 in presence of a base in a suitable solvent and optionally in presence of a suitable antioxidant to provide the compound of formula-1,
i) optionally purifying the compound of formula-1 from a suitable solvent to provide pure compound of formula-1.

The preferred embodiment of the present invention provides a novel process for the preparation of 1,3-Thiazol-5-ylmethyl[(2R,5R)-5-{[(2S)-2-[(methyl{[2-(propan-2-yl)-1,3-thiazol-4-yl]methyl} carbamoyl)amino]-4-(morpholin-4-yl)butanoyl]amino}-1,6-diphenylhexan-2-yl]carbamate compound of formula-1 comprising of:

a) Reacting L-methionine with bromoacetic acid in presence of acetic acid in the mixture of isopropanol and water to provide (S)-3-aminodihydrofuran-2(3H)-one compound of formula-3, further it is treating with isopropanolic-HCl in isopropanol to provide (S)-3-aminodihydrofuran-2(3H)-one hydrochloride compound of formula-3a,
b) reacting the compound of formula-3a with the 1-(2-isopropylthiazol-4-yl)-N-methylmethanamine dihydrochloride compound of formula-2a in presence of CDI and triethyl amine in dichloromethane to provide (S)-1-((2-isopropylthiazol-4-yl)methyl)-1-methyl-3-(2-oxotetrahydrofuran-3-yl)urea compound of formula-4,
c) treating the compound of formula-4 with sodium bromide and trimethyl silylchloride in methanol and followed by reacting the obtained compound with morpholine to provide a the compound of formula-5a,
d) treating the compound of formula-5a in-situ with oxalic acid to provide the compound of formula-6a,
e) basifying the compound of formula-6a using aqueous sodium bicarbonate solution and treating the obtained compound with aqueous potassium carbonate solution in dichloromethane to provide compound of formula-7a,
f) which on in-situ reacting with the compound of formula-8a$_1$ in presence of EDC.HCl, HOBT and diisopropyl ethylamine to provide the compound of formula-9a,
g) which on in-situ treating with hydrochloric acid in dichloromethane followed by treating with aqueous potassium carbonate solution to provide the compound of formula-10,
h) reacting the compound of formula-10 with the 4-nitrophenyl thiazol-5-ylmethyl carbonate compound of formula-13a in presence of diisopropyl ethyl amine in isopropanol to provide the compound of formula-1.

The above aspect of the present invention is schematically represented as follows:

Scheme-1

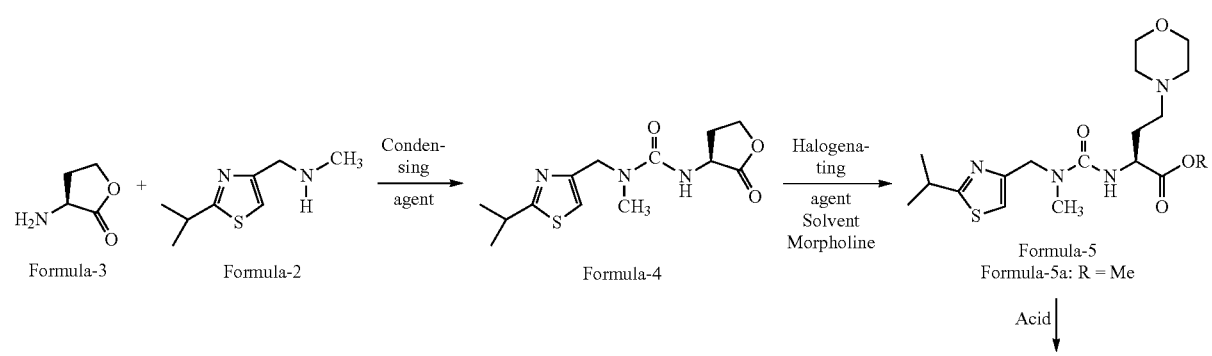

-continued
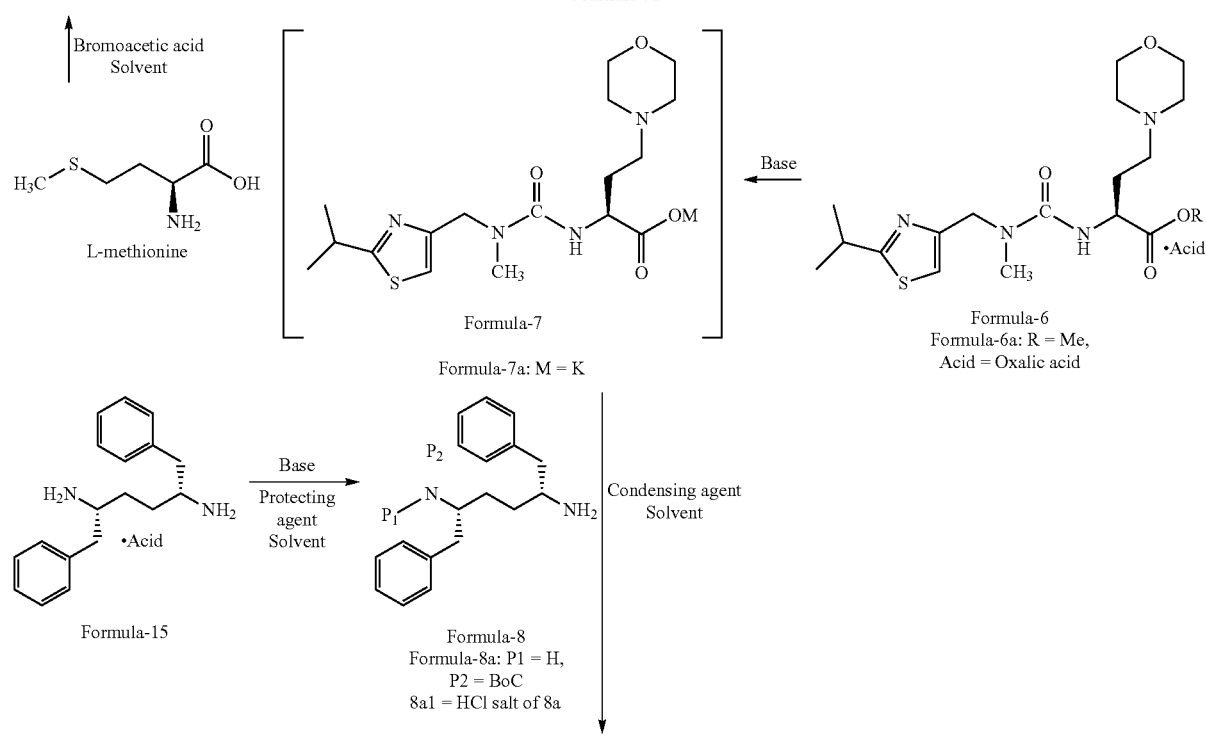
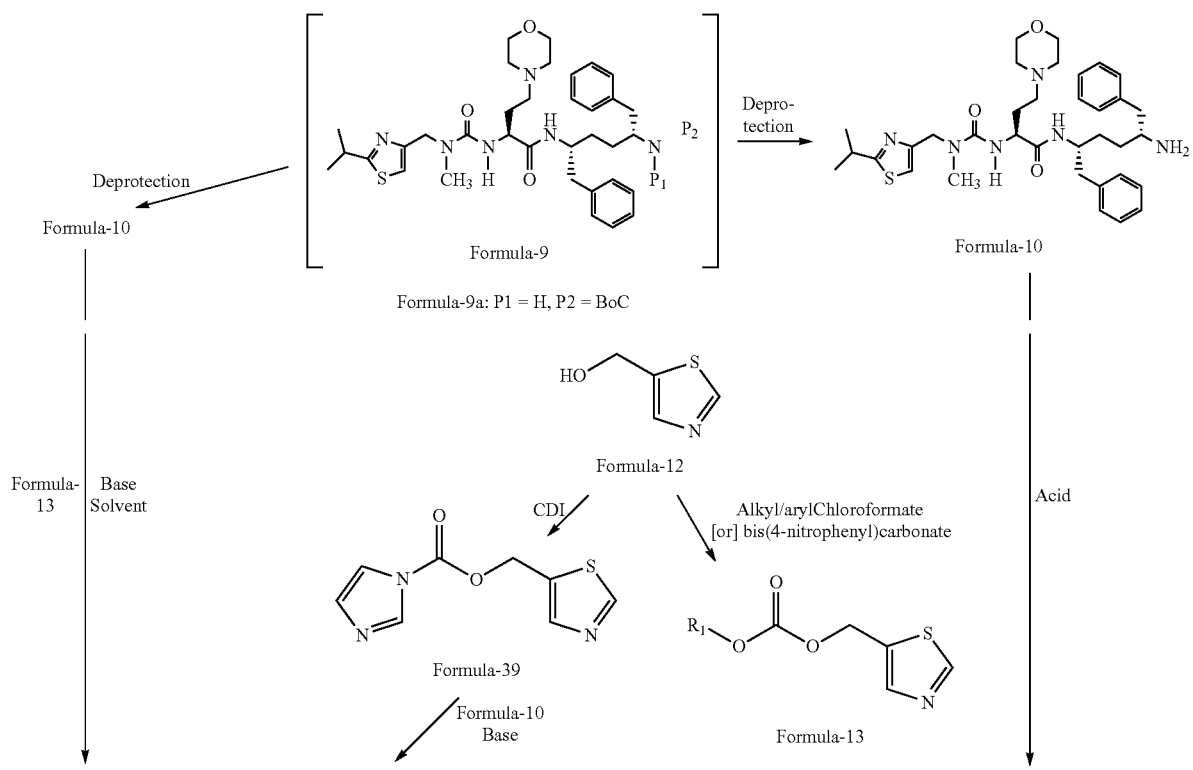

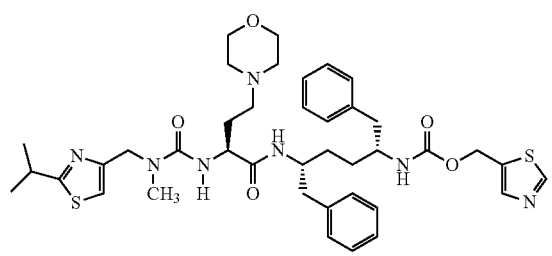

Formula-1

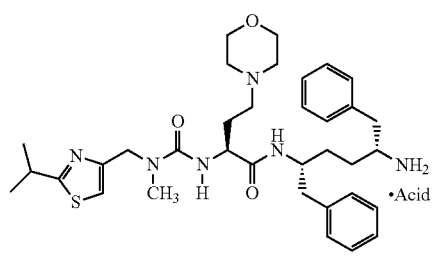

Formula-11
Formula-11a: Acid = HCl

Wherein
R = straight or branched chain alkyl, aralky, aryl, substituted aralkyl/aryl group
$R_1$ = straight or branched chain alkyl, aralkyl, aryl, substituted aralkyl/aryl group
P1, P2 are individually selected from H or amine protecting group with the proviso that P1 and P2 both are not 'H'; M = Na, K, Li, H Further the compound of formula-1 obtained above is converted to solid dispersion of cobicistat with silicondioxide, comprising of:
a) Dissolving the cobicistat compound of formula-1 in a suitable solvent,
b) adding silicon dioxide to the reaction mixture of step-a)
c) distilling the solvent from the reaction mixture,
d) adding a second solvent to the obtained compound in step-c),
e) isolating the solid dispersion of cobicistat with silicondioxide.

Wherein in step-a) a suitable solvent is selected from chloro solvents, preferably dichloromethane;
In step-d) the suitable second solvent is selected from hydrocarbon solvents; preferably hexane, heptane;
In step-e) isolating refers to the solvent removing by known techniques such as filtering, decanting or distilling.

Intermediate compounds of the present invention can be converted into their acid addition salts.

The second aspect of the present invention provides an improved process for the preparation of the compound of general formula-13 comprising of; reacting the thiazol-5-yl-methanol compound of formula-12 with a suitable alkyl or aryl haloformate in presence of a suitable base in a suitable solvent to provide the compound of general formula-12.

Wherein the alkyl or aryl haloformate are selected from methyl chloroformate, ethyl chloroformate, phenyl chloroformate, benzyl chloroformate; suitable base and suitable solvent are same as defined above.

The third aspect of the present invention provides a novel intermediate compound of the general formula-8 or their salts,

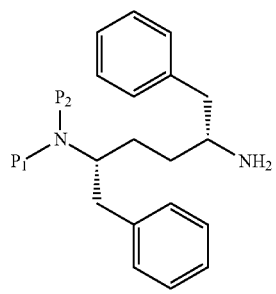

Formula-8

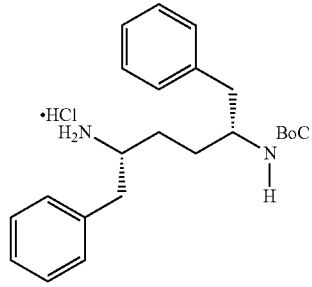

Formula-8a₁ wherein $P_1$, $P_2$ are individually selected from H or amine protecting group with the proviso that $P_1$ and $P_2$ both are not 'H'.

Figure 5:
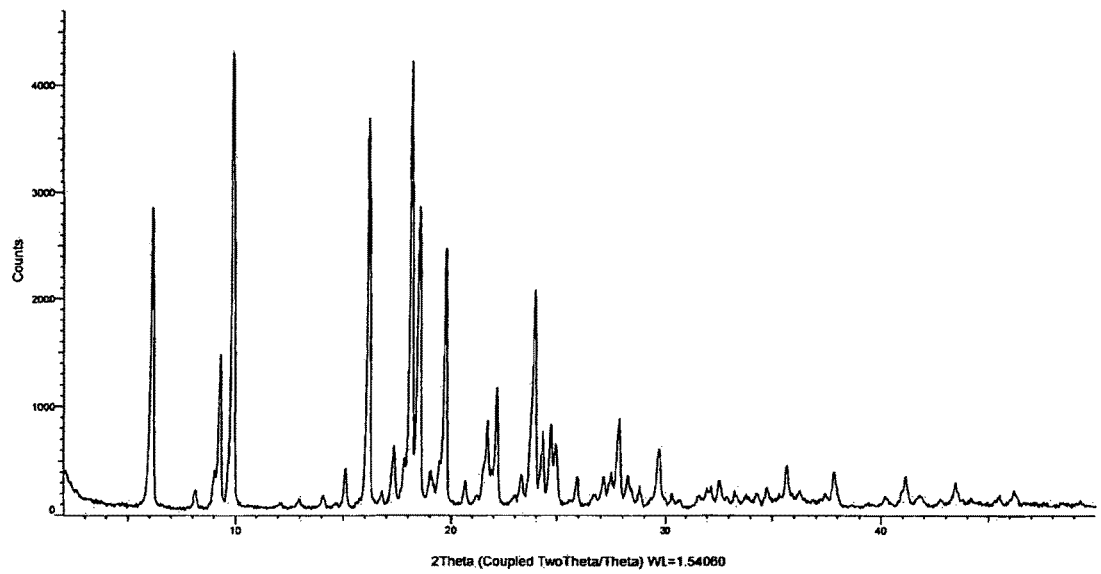
FIG. 5: Illustrates the PXRD pattern of crystalline form-M of the compound of formula-$8a_1$.

Preferred embodiment of the present invention provides a crystalline tert-butyl (2R,5R)-5-amino-1,6-diphenylhexan-2-yl-carbamate hydrochloride compound of formula-8a₁, herein after designated as crystalline form-M and which is characterized by:

Its powder X-Ray diffractogram having peaks at 6.14, 9.91, 16.20, 18.16, 18.52, 19.73, 22.15, 23.92±0.2 degrees of two theta and PXRD pattern as illustrated in fig-5.

Figure 6:
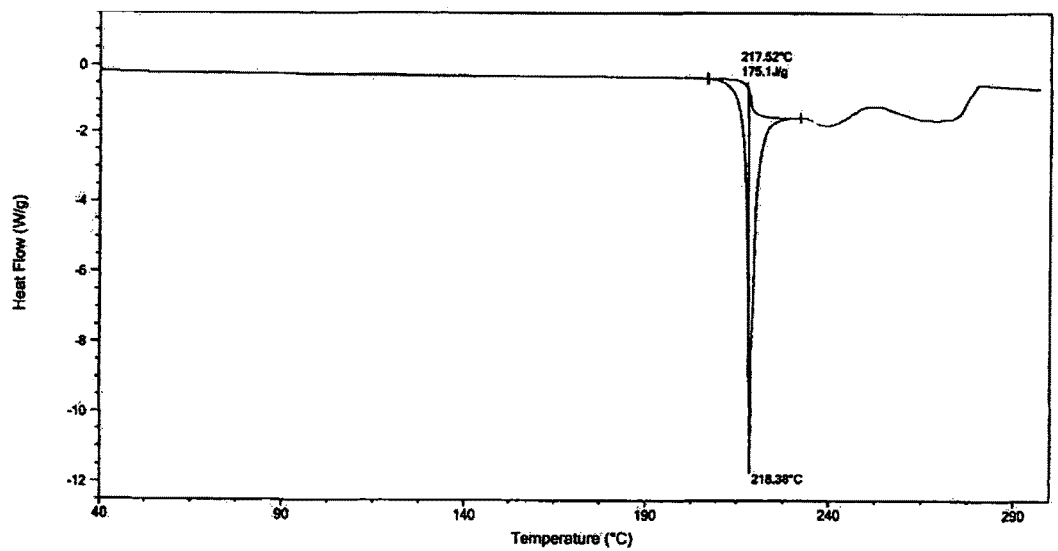
FIG. 6: Illustrates the DSC of crystalline form-M of the compound of formula-$8a_1$.

Its DSC thermogram showing an endotherm at 218.38° C. as illustrated in FIG. 6.

The fourth aspect of the present invention provides a process for the preparation of the compound of the general formula-8 or their salts, comprising of; treating the compound of formula-15 or its free base compound of formula-14

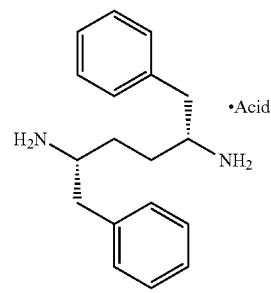

Formula-15 wherein the acid is selected from inorganic acids, organic acids or chiral acids; with suitable amino-protecting agents optionally in presence of a suitable base in a suitable solvent to provide the compound of general formula-8 or their salts, optionally purifying the compound of formula-8 or their salts.

The preferred embodiment of the present invention provides a process for the preparation of crystalline form-M of tert-butyl (2R, 5R)-5-amino-1,6-diphenylhexan-2-yl-carbamate hydrochloride, comprising of:
a) Treating the (2R, 5R)-1,6-diphenylhexane-2,5-diamine dihydrochloride with DIBOC in presence of triethyl amine in methanol to provide tert-butyl (2R, 5R)-5-amino-1,6-diphenylhexan-2-yl-carbamate;
b) treating the obtained compound in step-a) with ethyl acetate-HCl in ethyl acetate to provide the compound of formula-8a$_1$;
c) purifying the obtained compound in the mixture of ethyl acetate and water to provide the compound of formula-8a$_1$.

The compound of formula-8 or their salts obtained from the present invention are useful in the preparation of the compound of formula-1.

The fifth aspect of the present invention provides a solid dispersion of 1,3-thiazol-5-ylmethyl[(2R,5R)-5-{[(2S)2-[(methyl{[2-(propan-2-yl)-1,3-thiazol-4-yl] methyl}carbamoyl) amino]-4-(morpholin-4yl)butanoyl] amino}-1,6-diphenylhexan-2-yl]carbamate compound of formula-1 in combination with one or more pharmaceutically acceptable carrier.

In the present invention, the composition of the solid dispersion consist of a ratio of the amount of the compound of formula-1 to the amount of the pharmaceutically acceptable carrier therein ranges from about 1:0.1 to 1:10 by weight. The composition of Cobicistat with pharmaceutically acceptable carrier, preferably MCC, PVP, HPMC, HPC or HPMC-AS is about 1:0.1 to 1:10.

The sixth aspect of the present invention provides a solid dispersion of the compound of formula-1 in combination with cellulose derivatives.

Preferred embodiment of the present invention provides a solid dispersion of the compound of formula-1 in combination with microcrystalline cellulose.

Another preferred embodiment of the present invention provides a solid dispersion of the compound of formula-1 in combination with HPMC.

The seventh aspect of the present invention provides a process for the preparation of a solid dispersion of 1,3-thiazol-5-ylmethyl[(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenyl hexan-2-yl] carbamate compound of formula-1, comprising of the following steps:
a) Adding a suitable solvent to 1,3-thiazol-5-ylmethyl[(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenyl hexan-2-yl] carbamate,
b) adding a pharmaceutically acceptable carrier to the reaction mixture,
c) stirring the reaction mixture,
d) isolating the solid dispersion of 1,3-thiazol-5-ylmethyl [(2R,5R)-5-{[(2S)2-[(methyl{[2-(propan-2-yl)-1,3-thiazol-4-yl]methyl} carbamoyl)amino]-4-(morpholin-4yl) butanoyl] amino}-1,6-diphenylhexan-2-yl] carbamate compound of formula-1.

Wherein,
in step-a) the suitable solvent is selected from alcohol solvents, chloro solvents, ester solvents, polar aprotic solvents, ketone solvents, hydrocarbon solvents and polar solvent like water or mixture thereof;
in step-b) the suitable pharmaceutically acceptable carrier selected from cellulose derivatives such as cellulose acetate, cellulose nitrate, cellulose xanthate, carboxy methyl cellulose, micro crystalline cellulose, methyl cellulose, ethyl cellulose, and hydroxy ethyl cellulose; polyvinylpyrrolidone.
in step-d) isolation may be affected by removing the solvent. Suitable techniques which may be used for the removal of solvent include filtration, using a rotational distillation device such as a Buchi Rotavapor, spray drying, agitated thin film drying ("ATFD"), freeze drying (lyophilization), and the like or any other suitable technique.

The preferred embodiment of the present invention provides a process for the preparation of a solid dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl)butanoyl] amino}-1,6-diphenyl hexan-2-yl] carbamate compound of formula-1 in combination with MCC, comprising of the following steps:
a) Adding dichloromethane to 1,3-thiazol-5-ylmethyl [(2R, 5R)-5-{[(2S)2-[(methyl{[2-(propan-2-yl)-1,3-thiazol-4-yl]methyl}carbamoyl)amino]-4-(morpholin-4yl)butanoyl] amino}-1,6-diphenyl hexane-2-yl] carbamate,
b) adding micro crystalline cellulose to the reaction mixture,
c) stirring the reaction mixture,
d) distilling off the solvent completely from the reaction mixture to provide a solid dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenyl hexan-2-yl] carbamate compound of formula-1 with MCC.

Another preferred embodiment of the present invention provides a process for the preparation of an solid dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenylhexan-2-yl]carbamate compound of formula-1 in combination with HPMC, comprising of the following steps:
a) Adding dichloromethane to 1,3-thiazol-5-ylmethyl [(2R, 5R)-5-{[(2S)2-[(methyl{[2-(propan-2-yl)-1,3-thiazol-4-yl]methyl}carbamoyl)amino]-4-(morpholin-4yl)butanoyl] amino}-1,6-diphenyl hexan-2-yl] carbamate,
b) adding hydroxypropyl methylcellulose to the reaction mixture,
c) stirring the reaction mixture,
d) distilling off the solvent completely from the reaction mixture to provide solid dispersion of 1,3-thiazol-5-ylmethyl [(2R,5R)-5-{[(2S)2-[(methyl{[2-(propan-2-yl)-1,3-thiazol-4-yl] methyl}carbamoyl)amino]-4-(morpholin-4yl)butanoyl]amino}-1,6-diphenylhexan-2-yl] carbamate compound of formula-1 in combination with HPMC.

Preferred solid dispersions are "solid solutions", where the dispersion of the components is such that the system is chemically and physically uniform or homogeneous throughout or even consists of one phase as defined by measurement of thermodynamic properties of the system, e.g. cobicistat and a pharmaceutically acceptable carrier form a system that is chemically and physically uniform or homogeneous throughout or even consists of one phase as defined by measurement of thermodynamic properties of the system.

The eighth aspect of the present invention provides a novel process for the preparation of solid dispersion of cobicistat with silicondioxide comprising of:

a) Reacting the thiazol-5ylmethanol with CDI in presence of the suitable base in the suitable solvent to provide thiazol-5-ylmethyl 1H-imidazole-1-carboxylate compound of formula-39,

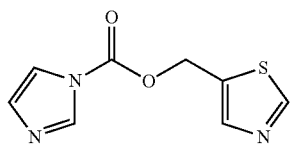

Formula-39 b) reacting the compound of formula-39 with the compound of formula-10,

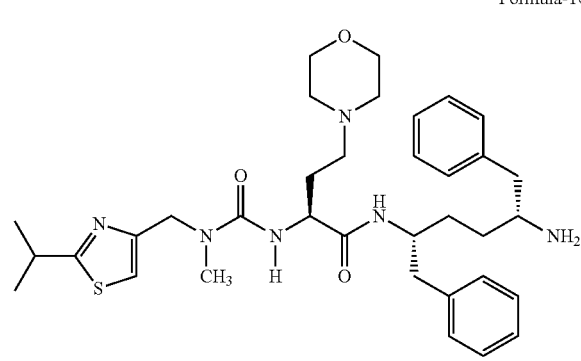

Formula-10 in presence of the suitable base in the suitable solvent to provide the compound of formula-1, c) adding silicondioxide to the compound of formula-1 in the suitable solvent, d) isolating the solid dispersion of cobicistat with silicondioxide.

Wherein in step-a), b) & c) the suitable solvent is selected from chloro solvents, hydrocarbon solvents, alcohol solvents or mixtures thereof; in step-a) & b) the suitable base is selected from organic base.

The preferred embodiment of the present invention provides a novel process for the preparation of solid dispersion of cobicistat with silicondioxide comprising of:

a) Reacting the thiazol-5ylmethanol with CDI in presence of triethyl amine dichloromethane to provide thiazol-5-ylmethyl 1H-imidazole-1-carboxylate compound of formula-39, b) reacting the compound of formula-39 with the compound of formula-10,

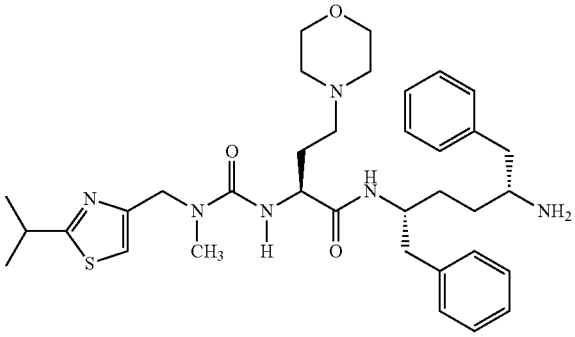

Formula-10 in presence of triethyl amine in dichloromethane to provide the compound of formula-1, c) adding silicondioxide to the compound of formula-1 in dichloromethane and n-heptane, d) isolating the solid dispersion of cobicistat with silicondioxide.

The invention also encompasses pharmaceutical compositions comprising a solid dispersion of 1,3-thiazol-5-ylmethyl [(2R,5R)-5-{[(2S)2-[(methyl {[2-(propan-2-yl)-1,3-thiazol-4-yl]methyl}carbamoyl)amino]-4-(morpholin-4yl) butanoyl]amino}-1,6-diphenyl hexan-2-yl]carbamate and one more pharmaceutical excipients. As used herein, the term "pharmaceutical compositions" or "pharmaceutical formulations" include tablets, pills, powders, liquids, suspensions, emulsions, granules, capsules, suppositories, or injection preparations.

Pharmaceutical compositions containing a solid dispersion of 1,3-thiazol-5-ylmethyl [(2R,5R)-5-{[(2S)2-[(methyl {[2-(propan-2-yl)-1,3-thiazol-4-yl]methyl}carbamoyl) amino]-4-(morpholin-4yl)butanoyl]amino}-1,6-diphenyl-hexan-2-yl]carbamate of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

HPLC Method of Analysis:

a) Cobicistat and its related substances were analyzed by HPLC with the following chromatographic conditions:

Apparatus: A liquid chromatograph is equipped with variable wavelength UV Detector. Column: Zobrax bonus RP, 250×4.6 mm, 5 gm (or) Equivalent; Wavelength: 235 nm; Column temperature: 30° C.; Injection volume: 20 µl; Diluent: Methanol & Water; Needle wash: Diluent; Elution: Gradient; Buffer: Transfer accurately 1.0 mL of perchloric acid into a 1000 mL of milli-Q-water, mix well and adjust pH=2.8 with diluted NaOH solution.

Mobile phase-A: Buffer; Mobile phase-B: Acetonitrile: Methanol:Buffer [75:5:20 v/v/v]

b) Tert-butyl (2R, 5R)-5-amino-1,6-diphenylhexan-2-yl-carbamate hydrochloride and its related substances were analyzed by HPLC with the following chromatographic conditions:

Apparatus: A liquid chromatograph is equipped with variable wavelength UV Detector. Column: Zobrax bonus RP, 250×4.6 mm, 5 gm (or) Equivalent; Wavelength: 215 nm; Column temperature: 40° C.; Injection volume: 10 µL; Diluent: Acetonitrile & Water; Needle wash: Diluent;

Elution: Gradient; Buffer: First filter 1000 mL of milli-Q-water then add 1.0 mL of perchloric acid and mix well.

Mobile phase-A: Buffer; Mobile phase-B: Acetonitrile:Methanol:Buffer [75:20:5 v/v/v]

c) (S)—N-((2R,5R)-5-amino-1,6-diphenylhexan-2-yl)-2-(3-((2-isopropylthiazol-4-yl)methyl)-3-methylureido)-4-morpholinobutanamide and its related substances were analyzed by HPLC with the following chromatographic conditions:

Apparatus: A liquid chromatograph is equipped with variable wavelength UV Detector. Column: Unison UK C18 UP, 100×2 mm, 3 μm (or) Equivalent; Wavelength: 215 nm; Column temperature: 40° C.; Injection volume: 2 μL; Diluent: 0.1% HClO4 in milli-Q-water:Methanol (1:1 v/v); Needle wash: Methanol; Elution: Gradient; Buffer: Weigh and transfer accurately 1.0 gm of 1-octane sulphonic acid sodium slt anhydrous in to a 1000 mL of milli-Q-water, mix well and filter. Then add 1 mL of perchloric acid and mix well.

Mobile phase-A: Buffer; Mobile phase-B: Acetonitrile:Buffer:Methanol [75:20:5 v/v/v]

Chiral HPLC Method of Analysis:

a) Cobicistat analyzed by Chiral Purity by HPLC with the following chromatographic conditions:

Apparatus: A liquid chromatograph is equipped with variable wavelength UV Detector. Column: Chiral Pack IA-3, 250×4.6 mm, 3 μm (or) Equivalent; Wavelength: 235 nm; Column temperature: 35° C.; Injection volume: 20 μL; Diluent: Mobile phase; Needle wash: Diluent; Elution: Isocratic; Mobile phase: n-hexane:MTBE:Ethanol:Dichloromethane:1-propanol: Trifluoro acetic acid: Ethanolamine [65:15:10:5:5:0.1:0.2 v/v/v/v/v/v/v]

b) Tert-butyl (2R, 5R)-5-amino-1,6-diphenylhexan-2-yl-carbamate hydrochloride by chiral purity with the following conditions:

Apparatus: A liquid chromatograph is equipped with variable wavelength UV Detector. Column: Chiral Pack IC-3, 250×4.6 mm (or) Equivalent; Wavelength: 215 nm; Column temperature: 30° C.; Injection volume: 15 μL; Diluent: Solution-A: Solution-B (75:25 v/v); Needle wash: Methanol; Elution: Isocratic;

Solution-A: n-hexane; Solution-B: Isopropanol:1-Propanol: Isopropylamine (600:400:2 v/v/v).

Mobile phase: Solution-A: Solution-B (90:10 v/v)-Premix

P-XRD Method of Analysis:

PXRD analysis of compounds produced by the present invention were carried out using BRUKER/AXS. X-Ray diffractometer using Cu Kα radiation of wavelength 1.5406 A° and continuous scan speed of 0.03°/min.

The following impurities are observed during the preparation of Cobicistat as per the present invention:

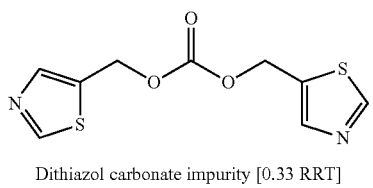

Dithiazol carbonate impurity [0.33 RRT]

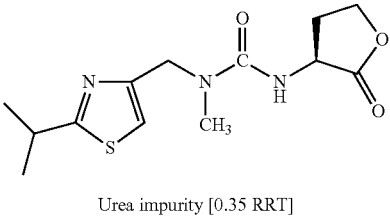

Urea impurity [0.35 RRT]

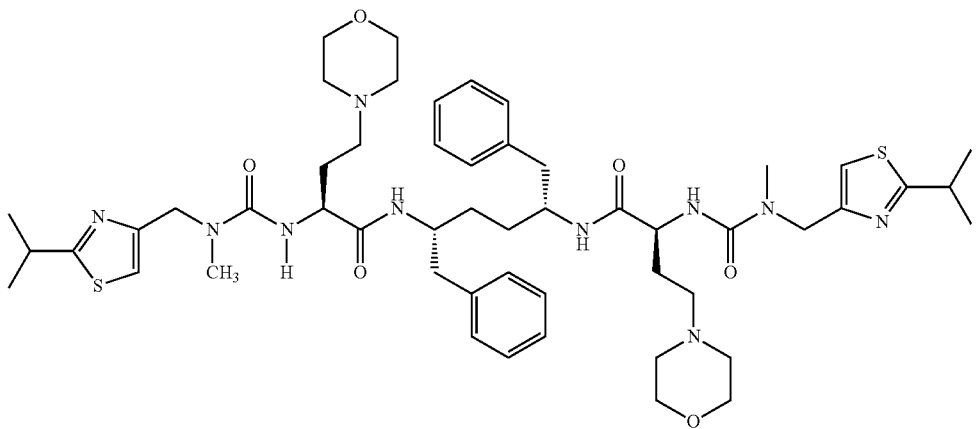

Dimorpholine impurity [0.85 RRT]

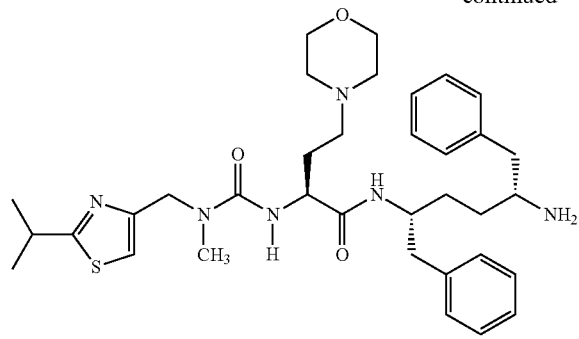
Morpholine amine impurity [0.46 RRT]
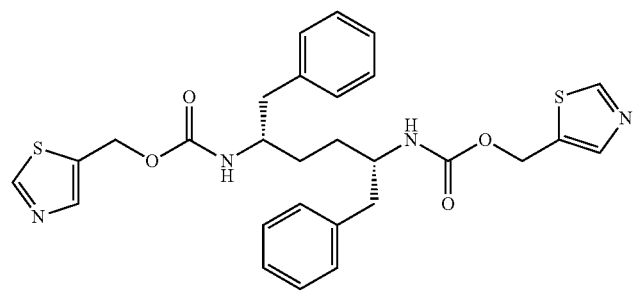
Dithiazolediamine impurity [1.43 RRT]
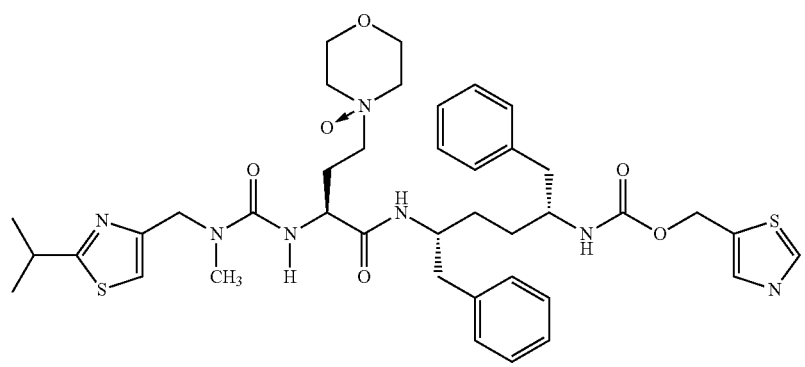
Morpholine N-Oxide impurity [1.04 RRT]
The process for the preparation of the compound of formula-14 or formula-15 of the present invention is schematically represented as follows:

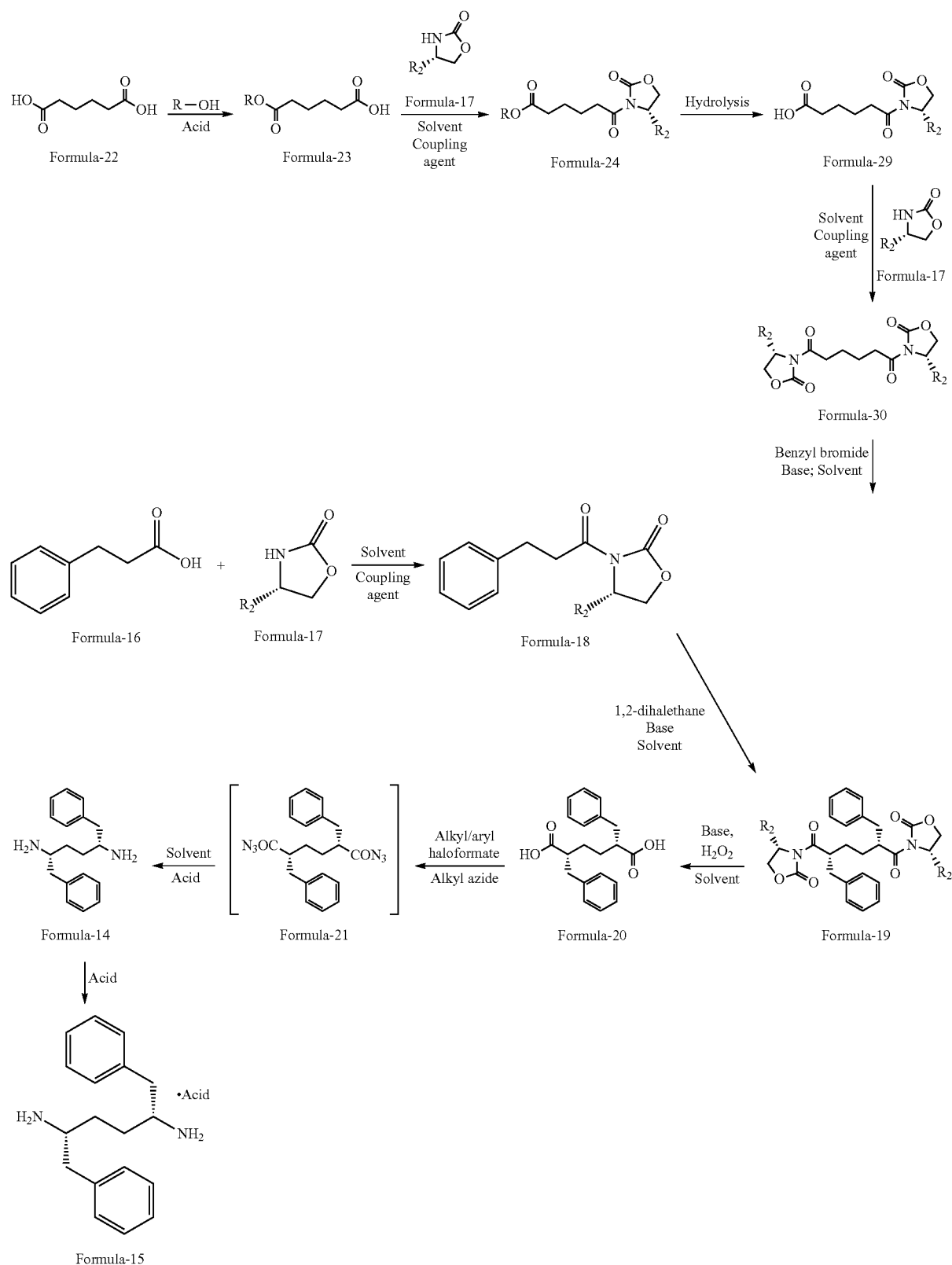

Scheme-3
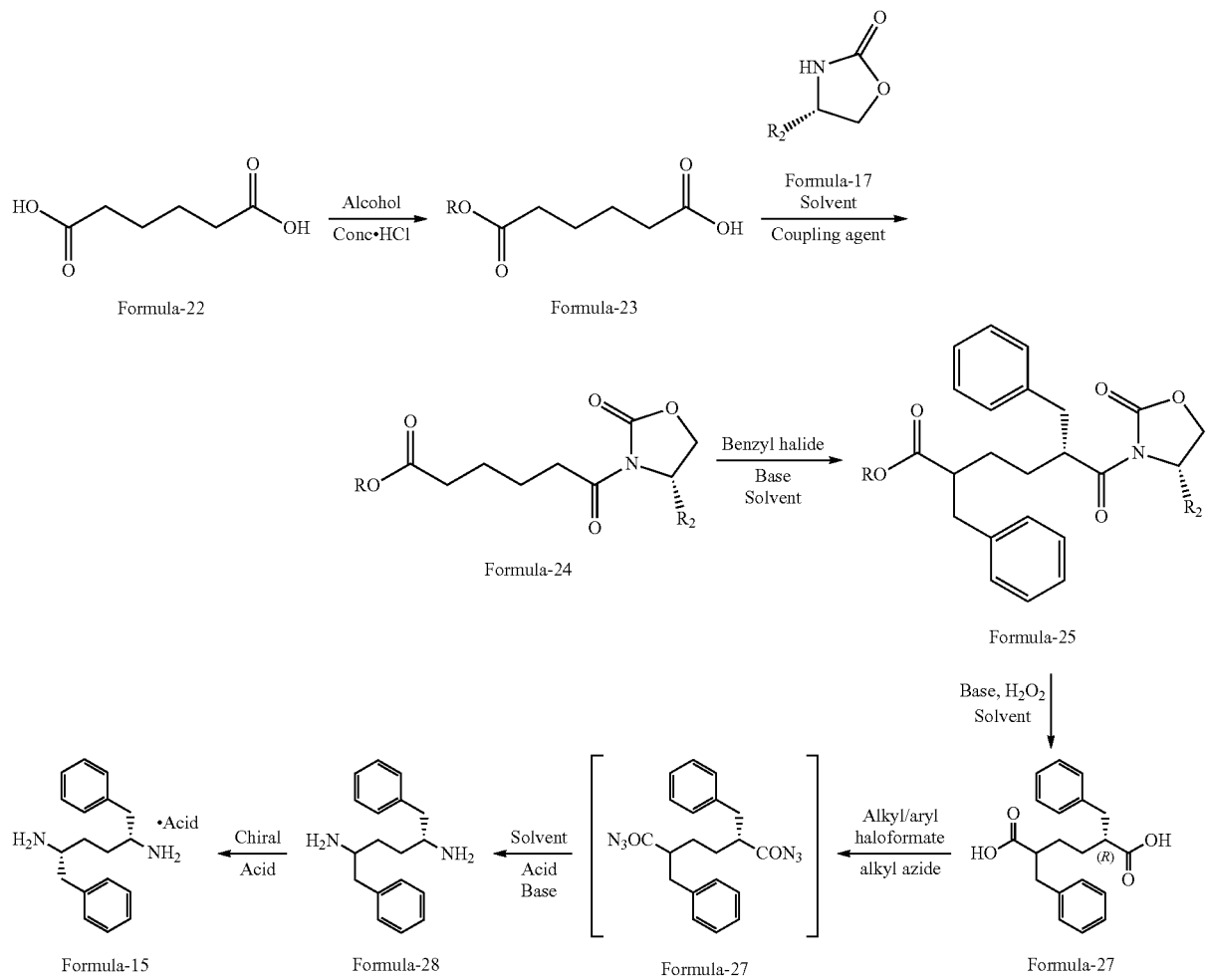
Wherein R & R₂ = straight or branched chain alkyl, aralkyl, aryl, substituted aralkyl/aryl group
Scheme-4
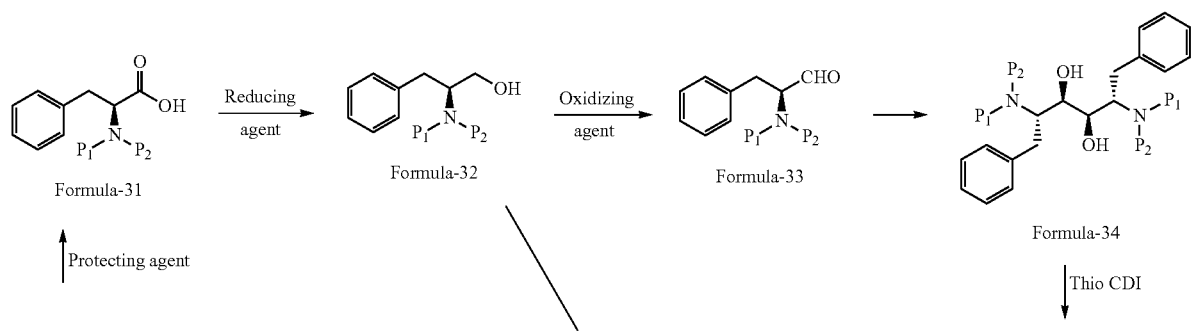

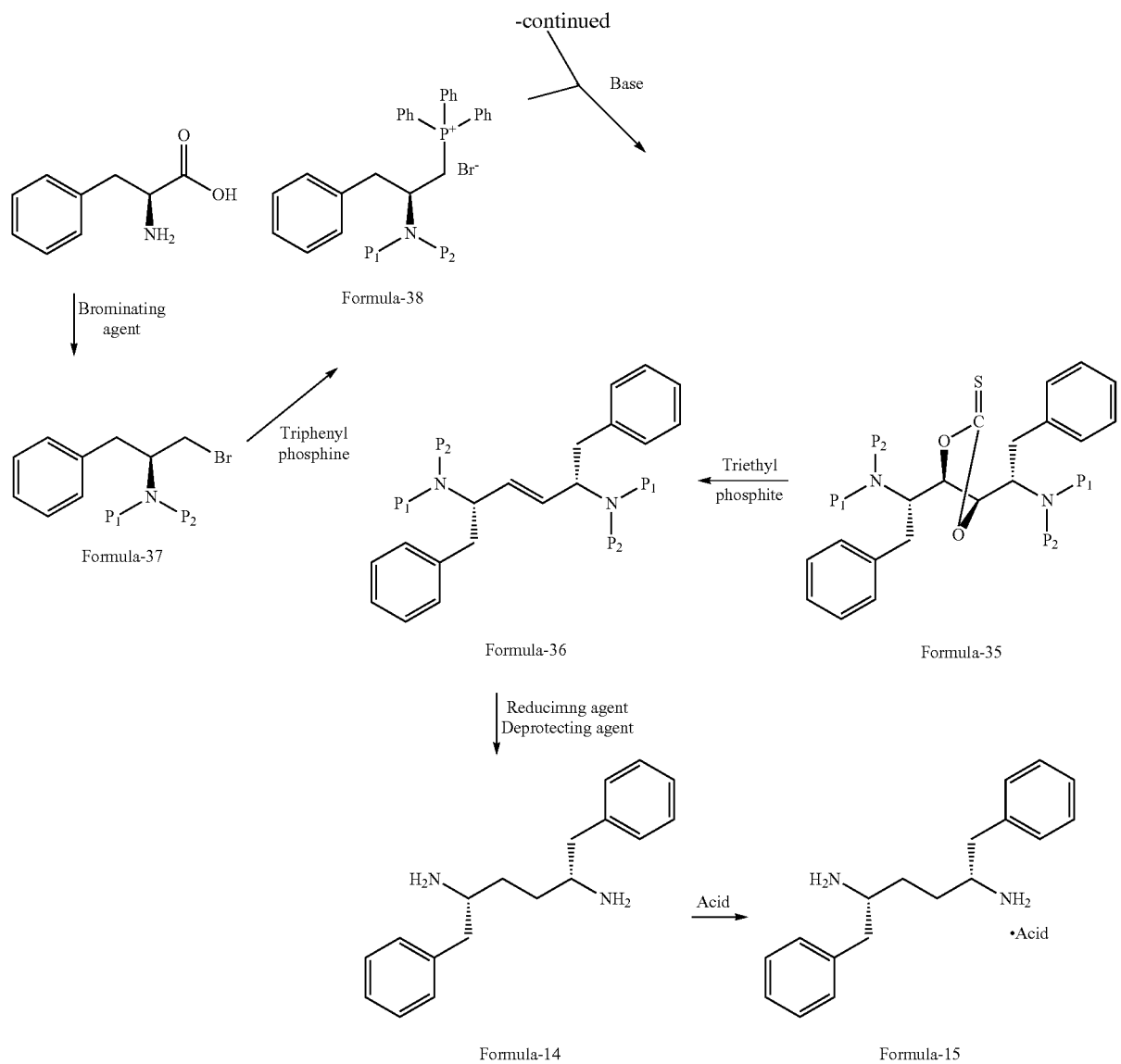

Wherein P1, P2 are individually selected from H or amine protecting group with the proviso that P1 and P2 both are not 'H'

EXAMPLES

The best mode of carrying out the present invention is illustrated by the below mentioned examples. These examples are provided as illustration only and hence should not be construed as limitation to the scope of the invention.

Example-1

Preparation of (S)-3-aminodihydrofuran-2(3H)-one hydrobromide Compound of Formula-3a A solution of L-methionine (50 gm) and water (75 ml) was added to a mixture of 2-bromoacetic acid (49.8 gm), isopropanol (95.4 ml) and acetic acid (71.5 ml) at 25-30° C. The reaction mixture was heated to 90-95° C. and stirred for 18 hrs at the same temperature. Distilled off the solvent completely under reduced pressure and co-distilled with isopropanol. Isopropanol (63.7 ml) and IPA.HCl (111 ml) were added to the obtained compound at 25-30° C. and stirred for 15 minutes at the same temperature. Heated the reaction mixture to 60-65° C. and stirred for 5 hours at the same temperature. Cooled the reaction mixture to 20-25° C. and stirred for 3 hours at the same temperature. Filtered the precipitated solid, washed twice with isopropanol and dried to get the title compound. Yield: 38.5 gm.

Example-2

Preparation of (S)-3-aminodihydrofuran-2(3H)-one hydrobromide Compound of Formula-3a A solution of L-methionine (100 gm) and water (150 ml) was added to a mixture of 2-bromoacetic acid (100 gm), isopropanol (200 ml) and acetic acid (150 ml) at 25-30° C. The reaction mixture was heated to 95-100° C. and stirred for 5 hrs at the same temperature. Distilled off the solvent completely under reduced pressure and co-distilled with isopropanol. Isopropanol (450 ml) and IPA.HCl (200 ml) were added to the obtained compound at 25-30° C. and stirred for 3 hrs at the same temperature. Filtered the precipitated solid, washed with isopropanol and dried to get the title compound. Yield: 80 gm; M.R.: 222-225° C.; SOR: $[\alpha]^{20}{}_D=(-)19.767°$ (C=1 in $H_2O$, UV 589 nm)

Example-3

Preparation of (S)-1-((2-isopropylthiazol-4-yl) methyl)-1-methyl-3-(2-oxotetra hydrofuran-3-yl) urea Compound of Formula-4

Carbonyldiimidazole (46.7 gm) and diisopropyl ethyl amine (106 gm) were added to a mixture of (S)-3-aminodihydrofuran-2-(3H)-one hydrobromide (50 gm) and dichloromethane (1000 ml) at 25-30° C. under nitrogen atmosphere. The reaction mixture was cooled to 15-20° C. and stirred for 10 hours at 15-20° C. 1-(2-isopropyl thiazol-4-yl)-N-methylmethanamine dihydrochloride (66.8 gm) was added to the reaction mixture at 15-20° C. and stirred for 12 hours at the same temperature. The temperature of the reaction mixture was raised to 25-30° C. Water was added to the reaction mixture at 25-30° C. and stirred for 15 minutes at the same temperature. Both the organic and aqueous layers were separated. Organic layer was washed with 20% citric acid solution followed by washed with aqueous sodium bicarbonate solution. Distilled off the solvent completely from the organic layer under reduced pressure to get the title compound. Yield: 71 gm.

Example-4

Preparation of (S)-1-((2-isopropylthiazol-4-yl) methyl)-1-methyl-3-(2-oxotetra hydrofuran-3-yl) urea Compound of Formula-4

A mixture of (S)-3-aminodihydrofuran-2-(3H)-one hydrobromide (100 gm) and dichloromethane (550 ml) was cooled to 0-5° C. under nitrogen atmosphere. Carbonyldiimidazole (100 gm) followed by triethylamine (49 gm) was slowly added to the reaction mixture at 0-5° C. and stirred it for 3 hrs the same temperature. 1-(2-isopropyl thiazol-4-yl)-N-methylmethanamine dihydrochloride (108.7 gm) followed by triethylamine (100 gm) was slowly added to the reaction mixture at 0-5° C. The temperature of the reaction mixture was raised to 25-30° C. and stirred for 6 hrs at the same temperature. Water was added to the reaction mixture at 25-30° C. and stirred for 15 minutes at the same temperature. Both the organic and aqueous layers were separated. Organic layer was washed with 20% acetic acid solution followed by washed with aqueous sodium bicarbonate solution and further washed with water. Distilled off the solvent completely from the organic layer under reduced pressure to get the title compound. Yield: 150 gm; HPLC Purity: 95.04%; Chiral purity: 99.46%, R-isomer: 0.54%.

Example-5

Preparation of (S)-methyl-2-(3-((2-isopropylthiazol-4-yl)methyl)-3-methyl ureido)-4-morpholinobutanoate oxalate Compound of Formula-6a Methanol (48 ml) was added to a mixture of (S)-1-((2-isopropylthiazol-4-yl)methyl)-1-methyl-3-(2-oxotetrahydrofuran-3-yl)urea (40 gm) and dichloromethane (200 ml) at 25-30° C. Sodium iodide (70.29 gm) was added to the reaction mixture at 25-30° C. and cooled it to 0-5° C. Trimethyl silyl chloride (67 gm) was slowly added to the reaction mixture at 0-5° C. Temperature of the reaction mixture was raised to 20-25° C. and stirred for 6 hrs at 20-25° C. Cooled the reaction mixture to 0-5° C. Morpholine (117.5 ml) was slowly added to the reaction mixture at 0-5° C. and temperature of the reaction mixture was raised to 20-25° C. Stirred the reaction mixture for 12 hrs at 20-25° C. Filtered the reaction mixture and washed with dichloromethane. Distilled off the solvent from the filtrate completely under reduced pressure and co-distilled with ethyl acetate. Ethyl acetate (200 ml) was added to the obtained compound and stirred at 25-30° C. for 20 minutes. A solution of Oxalic acid (25.4 gm) dissolved in acetone (200 ml) was added to the reaction mixture at 25-30° C. and stirred for 3 hrs at the same temperature. The obtained solid was filtered, washed with the mixture of ethyl acetate and acetone and dried to get the title compound. Yield: 67.71 gm.

Example-6

Preparation of (S)-methyl-2-(3-((2-isopropylthiazol-4-yl)methyl)-3-methyl ureido)-4-morpholinobutanoate oxalate Compound of Formula-6a ($R=CH_3$, Acid=Oxalic Acid)

Sodium bromide (173 gm) was added to a mixture of (S)-1-((2-isopropylthiazol-4-yl)methyl)-1-methyl-3-(2-oxotetrahydrofuran-3-yl)urea (100 gm), methanol (120 ml) and dichloromethane (1000 ml) at 25-30° C. under nitrogen atmosphere. Trimethyl silyl chloride (182.6 gm) was slowly added to the reaction mixture at 25-30° C. and stirred for 6 hrs at the same temperature. Cooled the reaction mixture to 0-5° C. Morpholine (293 ml) was slowly added to the reaction mixture at 0-5° C. and temperature of the reaction mixture was raised to 25-30° C. Stirred the reaction mixture for 12 hrs at 25-30° C. Filtered the reaction mixture and washed with dichloromethane. Water was added to the filtrate and stirred for 20 minutes. Both the organic and aqueous layers were separated. Organic layer was washed with water followed by washed with aqueous sodium bicarbonate solution. Distilled off the solvent from the organic layer completely under reduced pressure and co-distilled with isopropanol. Isopropanol (400 ml) was added to the obtained compound and stirred for 20 minutes at 25-30° C. A solution of Oxalic acid (42.4 gm) dissolved in isopropanol (600 ml) was added to the reaction mixture at 25-30° C. and stirred for 3 hrs at the same temperature. The obtained solid was filtered, washed with isopropanol and dried to get the title compound; Yield: 80.5 gm; M.R.: 130-135° C.; HPLC Purity: 98.40%; Chiral purity: 99.27%, R-isomer: 0.73%.

Example-7

Preparation of 6-methoxy-6-oxohexanoic acid Compound of Formula-23a ($R=CH_3$)

Conc.HCl (8.6 ml) was added to a mixture of adipic acid compound of formula-22 (100 gm) and methanol (27.7 ml) at 25-30° C. The reaction mixture was heated to 80-85° C. and stirred for 8 hrs at the same temperature. Cooled the reaction mixture to 25-30° C. Toluene (100 ml) was added to the reaction mixture and stirred for 45 minutes at 25-30° C. Filtered the reaction mixture and washed with toluene. Water was added to the filtrate. Basifying the reaction mixture with aqueous sodium carbonate solution. Both the organic and aqueous layers were separated and aqueous layer was washed with toluene. Dichloromethane was added to the aqueous layer. Acidifying the reaction mixture using Conc.HCl. Both the organic and aqueous layers were separated. Aqueous layer was extracted with dichloromethane and distilled off the solvent from the organic layer completely under reduced pressure to get the title compound; Yield: 109.6 gm.

Example-8

Preparation of (S)-methyl-6-oxo-6-(2-oxo-4-phenyloxazolidin-3-yl)hexanoate Compound of Formula-24a (R=CH$_3$, R$_2$=Ph)

(S)-4-phenyloxazolidin-2-one compound of formula-17a (33.86 gm) and DMAP (2.77 gm) was added to a mixture of 6-methoxy-6-oxohexanoic acid (35 gm) and dichloromethane (175 ml) at 25-30° C. DCC (54.13 gm) was slowly added to the reaction mixture at 25-30° C. and stirred the reaction mixture for 5 hrs at the same temperature. Cooled the reaction mixture to 0-5° C. and stirred for 60 minutes at the same temperature. The obtained unwanted solid was filtered. Washed the filtrate with 5% dilute HCl solution, followed by with water. Further washed the organic layer with 5% aqueous sodium carbonate solution followed by with water. Distilled off the solvent from the organic layer completely under reduced pressure. Pet ether was added to the obtained compound at 25-30° C. and stirred for 2 hrs at 25-30° C. The obtained solid was filtered, washed with pet ether and dried to get the title compound. Yield: 66.7 gm.

Example-9

Preparation of (S)-6-oxo-6-(2-oxo-4-phenyloxazolidin-3-yl)hexanoic acid Compound of Formula-29a (R$_2$=pH)

A mixture of (S)-methyl-6-oxo-6-(2-oxo-4-phenyloxazolidin-3-yl)hexanoate (15 gm) and acetonitrile (75 ml) was cooled to 0-5° C. Conc.HCl (45 ml) was slowly added to the reaction mixture, raised the temperature to 25-30° C. and stirred for 24 hrs at the same temperature. Distilled off the solvent completely from the reaction mixture. Cooled the reaction mixture to 25-30° C., added water and ethyl acetate. Basifying the reaction mixture using 20% aqueous sodium carbonate solution. Both the organic and aqueous layers were separated and aqueous layer was washed with ethyl acetate. Ethyl acetate was added to the aqueous layer and acidifying the reaction mixture using Conc.HCl and separated the layers. Distilled off the solvent completely from the organic layer under reduced pressure to get the title compound. Yield: 14.3 gm Example-10

Preparation of 1,6-bis((S)-2-oxo-4-phenyloxazolidin-3-yl)hexane-1,6-dione Compound of Formula-30a (R$_2$=pH)

(S)-4-phenyloxazolidin-2-one (5.32 gm) and DMAP (0.44 gm) were added to a mixture of (S)-6-oxo-6-(2-oxo-4-phenyloxazolidin-3-yl)hexanoic acid (10 gm) and dichloromethane (50 ml) at 25-30° C. DCC (9.2 gm) was slowly added to the reaction mixture at 25-30° C. and stirred the reaction mixture for 5 hrs at the same temperature. Cooled the reaction mixture to 0-5° C. and stirred for 60 minutes at the same temperature. The obtained unwanted solid was filtered. Washed the filtrate with 5% dilute HCl solution, followed by with water. Further washed the organic layer with 5% aqueous sodium carbonate solution followed by with water. Distilled off the solvent completely from the organic layer under reduced pressure to get the title compound. Yield: 14.9 gm.

Example-11

Preparation of (2R, 5R)-2,5-dibenzyl-1,6-bis((S)-2-oxo-4-phenyloxazolidin-3-yl)hexane-1,6-dione Compound of Formula-19a (R$_2$=pH)

A mixture of 1,6-bis((S)-2-oxo-4-phenyloxazolidin-3-yl) hexane-1,6-dione (5 gm) and tetrahydrofuran (25 ml) was cooled to −75° C. to −70° C. and NaHMDS (4.2 gm) was slowly added to the above reaction mixture. Stirred the reaction mixture for 30 minutes at the same temperature. Benzyl bromide (3.92 gm) in tetrahydrofuran (5 ml) was slowly added to the reaction mixture at −75° C. to −70° C. Raised the temperature of the reaction mixture to 25-30° C. and stirred for 4 hrs at the same temperature. Cooled the reaction mixture to 0-5° C. and quenched with aqueous ammonium chloride solution. The reaction mixture was extracted with ethyl acetate. The ethyl acetate layer was washed with aqueous sodium chloride solution and distilled off the solvent under reduced pressure to get the title compound. Yield: 7.09 gm.

Example-12

Preparation of (2R, 5R)-2,5-dibenzylhexanedioic acid Compound of Formula-20

A mixture of (2R, 5R)-2,5-dibenzyl-1,6-bis((S)-2-oxo-4-phenyloxazolidin-3-yl)hexane-1,6-dione (10 gm) and tetrahydrofuran (70 ml) was stirred at 0-5° C. for 15 minutes. Hydrogen peroxide in water (2.48 gm) was added to the reaction mixture at 0-5° C. Lithium hydroxide monohydrate (1.36 gm) was slowly added to the reaction mixture at 0-5° C. and stirred for 2 hrs at the same temperature. Quenched the reaction mixture with aqueous sodium sulfite solution. Raised the temperature of the reaction mixture to 25-30° C. The reaction mixture was washed with dichloromethane. Acidifying the reaction mixture with dilute HCl at 25-30° C. Ethyl acetate was added to the reaction mixture and stirred for 10 minutes. Both the organic and aqueous layers were separated and the aqueous layer was extracted with ethyl acetate. Distilled off the solvent completely under reduced pressure to get the title compound. Yield: 5.29 gm Example-13

Preparation of (2R, 5R)-1,6-diphenylhexane-2,5-diamine mandelate Compound of Formula-15a (Acid=Mandelic Acid)

A mixture of (2R, 5R)-2,5-dibenzylhexanedioic acid (5 gm), acetone (45 ml) and water (5 ml) was cooled to 0-5° C. Triethylamine (6.75 gm) and ethyl chloroformate (7.64 gm) was slowly added to the reaction mixture at 0-5° C. Stirred the reaction mixture for 1½ hours at the same temperature. A solution of Sodium azide (4.9 gm) dissolved in water were slowly added to the reaction mixture at 0-5° C. and stirred the reaction mixture for 3 hours at the same temperature. Toluene and water was added to the reaction mixture. Both the organic and aqueous layers were separated and the aqueous layer was extracted with toluene. Heated the organic layer to 100-105° C. and stirred for 3 hrs at the same temperature. Cooled the reaction mixture to 25-30° C. Conc. HCl (21 ml) mixed with water (14 ml) was added to the reaction mixture. Heated the reaction mixture to 85-90° C. and stirred for 3 hrs at the same temperature. Cooled the reaction mixture to 25-30° C. and stirred for 15 minutes at the same temperature. Both the organic and aqueous layers were separated and the aqueous layer was washed with toluene. Basifying the reaction mixture with aqueous sodium hydroxide solution. Ethyl acetate was added to the reaction mixture. Both the organic and aqueous layers were separated and the aqueous layer was extracted with ethyl acetate. The organic layer was washed with aqueous sodium chloride solution and distilled off the solvent completely from organic layer under reduced pressure. The residue obtained was dissolved in ethyl acetate. L(+) Madelic acid (2.32 gm) dissolved in ethyl acetate was slowly added to the reaction mixture at 20-25° C. and stirred for 6 hours at the same temperature. Filtered the precipitated solid, washed with ethyl acetate and dried to get the title compound. Yield: 3.0 gm.

Example-14

Preparation of Tert-butyl (2R, 5R)-5-amino-1,6-diphenylhexan-2-yl-carbamate Compound of Formula-8a ($P_1$=H, $P_2$=BOC)

A mixture of (2R, 5R)-1,6-diphenylhexane-2,5-diamine-2-hydroxy-2-phenylacetate (10 gm), dichloromethane (100 ml) and water (50 ml) was cooled to 5-10° C. Basifying the reaction mixture with aqueous potassium carbonate solution. The reaction mixture was stirred for 30 minutes at 5-10° C. Both the organic and aqueous layers were separated and the aqueous layer was extracted with dichloromethane. The organic layer was washed with water and dried over sodium sulphate. Triethylamine (4.97 ml) and DiBOC (2.59 gm) were added to the organic layer at 25-30° C. and stirred for 4 hrs at the same temperature. Water was added to the reaction mixture and stirred for 30 minutes at 25-30° C. Both the organic and aqueous layers were separated and the organic layer was washed with aqueous sodium chloride solution. Distilled off the solvent completely from the organic layer under reduced pressure to get the title compound. Yield: 10.79 gm.

Example-15

Preparation of Tert-butyl (2R, 5R)-5-amino-1,6-diphenylhexan-2-yl-carbamate hydrochloride Compound of Formula-$8a_1$ Triethyl amine (29.64 gm) was slowly added to a mixture of (2R, 5R)-1,6-diphenylhexane-2,5-diamine dihydrochloride (100 gm), methanol (600 ml) at 25-30° C. and stirred for 10 minutes. A solution of DiBOC (57.35 gm) in methanol (50 ml) was added to the above reaction mixture at 25-30° C. and stirred for 3 hrs. Dichloromethane followed by water was added to the reaction mixture and stirred for 15 minutes at 25-30° C. Both the organic and aqueous layers were separated and the organic layer was washed water. Distilled off the solvent completely from the organic layer under reduced pressure and co-distilled with ethyl acetate. Ethyl acetate (600 ml) was added to the obtained compound and cooled to 5-10° C. Ethyl acetate-HCl (100 ml) was slowly added to the reaction mixture at 5-10° C. and stirred it for 3 hrs. Filtered the precipitated solid and washed with ethyl acetate. The obtained compound was slurried in the mixture of water and ethyl acetate. Filtered solid and washed with ethyl acetate and dried to get the title compound. Yield: 60.5 gm; M.R..: 217-219° C., HPLC Purity: 99.65%; Chiral purity: 99.98%, S,S-isomer: 0.02%.

The PXRD pattern of the obtained compound is illustrated in FIG. 5 and its DSC in FIG. 6.

Example-16

Preparation of (S)—N-((2R,5R)-5-amino-1,6-diphenylhexan-2-yl)-2-(3-((2-isopropylthiazol-4-yl) methyl)-3-methylureido)-4-morpholinobutanamide hydrochloride Compound of Formula-11a (Acid=HCl)

Water (50 ml) was added to a mixture of (S)-methyl-2-(3-((2-isopropylthiazol-4-yl)methyl)-3-methylureido)-4-morpholinobutanoate oxalate (13.25 gm) and dichloromethane (100 ml) at 25-30° C. Cooled the reaction mixture to 10-15° C. Basifying the reaction mixture with aqueous sodium bicarbonate solution. The reaction mixture was stirred for 30 minutes at 10-15° C. Both the organic and aqueous layers were separated and the aqueous layer was extracted with dichloromethane. The organic layer was washed with water, dried over sodium sulphate and distilled off the solvent completely under reduced pressure. Ethanol (50 ml) was added the above obtained compound at 25-30° C. and stirred for 20 minutes at the same temperature. Cooled the reaction mixture to 5-10° C. A solution of potassium hydroxide (2.57 gm) dissolved in water was slowly added to the reaction mixture at 5-10° C. and stirred for 3 hrs at the same temperature. Distilled off the solvent completely under reduced pressure and co-distilled with dichloromethane. Dichloromethane was added to the obtained compound and stirred for 15 minutes at 25-30° C. Tert-butyl (2R, 5R)-5-amino-1,6-diphenylhexan-2-yl-carbamate (10 gm) in dichloromethane, HOBT (4.4 gm), EDC.HCl (7.7 gm) and diisopropylethylamine (7 ml) were added to the reaction mixture at 25-30° C. and stirred for 18 hrs at the same temperature. Water was added to the reaction mixture and stirred for 30 minutes at 25-30° C. Both the organic and aqueous layers were separated and the organic layer was washed with water and aqueous citric acid solution. Distilled off the solvent completely from the organic layer under reduced pressure. Ethyl acetate was added to the obtained compound and cooled to 5-10° C. Conc.HCl was slowly added to the reaction mixture at 5-10° C. Raised the temperature of the reaction mixture to 25-30° C. and stirred for 3 hrs at the same temperature. Water was added to the reaction mixture and stirred for 20 minutes at 25-30° C. Both the organic and aqueous layers were separated and the aqueous layer was extracted with ethyl acetate. The organic layer was washed with aqueous sodium carbonate solution followed by with aqueous sodium chloride solution and cooled the organic layer to 5-10° C. Acidifying the reaction mixture with ethyl acetate.HCl solution and stirred for 4 hrs at 5-10° C. Filtered the precipitated solid, washed with ethyl acetate and dried to get the title compound. Yield: 18.21 gm.

Example-17

Preparation of (S)—N-((2R,5R)-5-amino-1,6-diphenylhexan-2-yl)-2-(3-((2-isopropylthiazol-4-yl) methyl)-3-methylureido)-4-morpholinobutanamide Compound of Formula-10

Water (250 ml) was added to a mixture of (S)-methyl-2-(3-((2-isopropylthiazol-4-yl)methyl)-3-methylureido)-4- morpholinobutanoate oxalate (90.5 gm) and dichloromethane (500 ml) at 25-30° C. Cooled the reaction mixture to 10-15° C. Basifying the reaction mixture with aqueous sodium bicarbonate solution. The reaction mixture was stirred for 30 minutes at 10-15° C. Both the organic and aqueous layers were separated and the aqueous layer was extracted with dichloromethane. Combined the organic layers and washed with water and distilled off the solvent completely under reduced pressure. Dichloromethane (150 ml) was added the above obtained compound at 25-30° C. and cooled the reaction mixture to 5-10° C. A solution of potassium hydroxide (15.8 gm) dissolved in 18 ml of water was slowly added to the reaction mixture at 5-10° C. and stirred for 5 hrs at the same temperature. Dichloromethane (500 ml) was added to the reaction mixture at 5-10° C. and cooled to 0-5° C. Tert-butyl (2R, 5R)-5-amino-1,6-diphenylhexan-2-yl-carbamate hydrochloride (50 gm) and diisopropylethylamine (36.5 ml) were added to the reaction mixture at 0-5° C. and stirred for 60 minutes at the same temperature. HOBT (23.35 gm) was added to the above reaction mixture at 0-5° C. and stirred for 60 minutes at the same temperature. A solution of EDC.HCl (40.2 gm) in 500 ml of dichloromethane was slowly added to the above reaction mixture at 0-5° C. Raised the temperature of the reaction mixture to 5-10° C. and stirred for 12 hrs at the same temperature. Water was added to the reaction mixture and stirred for 30 minutes at 5-10° C. Both the organic and aqueous layers were separated and the organic layer was washed with aqueous potassium carbonate solution and followed by water. Cooled the organic layer to 0-5° C. and hydrochloric acid (300 ml) was slowly added to the reaction mixture at the same temperature. Raised the temperature of the reaction mixture to 25-30° C. and stirred for 6 hrs at the same temperature. Separated both the organic and aqueous layers and extracted the product using water from the organic layer. Combined the aqueous layers and washed the aqueous layer with dichloromethane. Dichloromethane was added to the aqueous layer and cooled to 0-5° C. Basified the reaction mixture using aqueous potassium carbonate solution and stirred for 30 minutes at the same temperature. Both the organic and aqueous layers were separated and aqueous layer was extracted with dichloromethane. Combined the organic layers at 25-30° C. and washed with water followed by with aqueous citric acid solution and then washed with water. Distilled off the solvent completely from the organic layer under reduced pressure and get the title compound. Yield: 95 gm; HPLC Purity: 96.74%.

Example-18

Preparation of 4-nitrophenyl thiazol-5-ylmethyl carbonate Compound of Formula-13a
[R=4-Nitrophenyl]

100 gm of thiazol-5-yl methanol was dissolved in 850 ml of dichloromethane at 25-30° C. Triethylamine (151.3 ml) and bis(4-nitrophenyl)carbonate (264.2 gm) was added to the reaction mixture and stirred the reaction mixture for 3 hrs at 25-30° C. Water was added to the reaction mixture and stirred for 20 minutes. Separated both the aqueous and organic layers. 30% aqueous sodium carbonate solution was added to the organic layer and stirred the reaction mixture. Filtered the obtained byproduct and washed with dichloromethane. Separated both the aqueous and organic layers from the filtrate. The organic layer was washed with water followed by aqueous sodium chloride solution. Distilled off the solvent from the organic layer and co-distilled with isopropanol. Isopropanol (200 ml) was added to the obtained compound and stirred the reaction mixture for 2 hrs at 25-30° C. Filtered the solid, washed with isopropanol and dried to get the title compound. Yield: 135.5 gm; M.R: 80-83° C.; Purity by HPLC: 99.53%.

Example-19

Preparation of thiazol-5-ylmethyl (2R, 5R)-5-((S)-2-(3-((2-isopropylthiazol-4-yl)methyl)-3-methylureido)-4-morpholinobutanamido)-1,6-diphenyl-hexan-2ylcarbamate Compound of Formula-1

Water (2.5 ml) was added to a mixture of (S)—N-((2R, 5R)-5-amino-1,6-diphenylhexan-2-yl)-2-(3-((2-isopropylthiazol-4-yl)methyl)-3-methylureido)-4-morpholinobutanamide hydrochloride (0.25 gm) and dichloromethane (2.5 ml). Cooled the reaction mixture to 5-10° C. Basifying the reaction mixture with aqueous sodium carbonate solution and stirred for 20 minutes at 5-10° C. Both the organic and aqueous layers were separated and the aqueous layer was extracted with dichloromethane. The organic layer was washed with water. 4-nitrophenyl thiazol-5-ylmethyl carbonate (0.08 gm) and diisopropylethylamine (0.097 ml) were added to the organic layer at 25-30° C. and stirred for 15 hrs at the same temperature. Water was added to the reaction mixture and stirred for 20 minutes at 25-30° C. Both the organic and aqueous layers were separated. Organic layer was washed with aqueous sodium carbonate solution and followed by with 5% aqueous citric acid solution. Cooled the organic layer to 5-10° C. Acidifying the reaction mixture with 20% aqueous citric acid solution. Separated both the organic and aqueous layers. Basifying the reaction mixture with aqueous sodium carbonate solution. Dichloromethane was added to it and separated both the organic and aqueous layers. The aqueous layer was extracted with dichloromethane and combined the organic layers. Distilled off the solvent completely from the organic layer under reduced pressure to get the title compound. Yield: 0.29 gm.

Example-20

Preparation of Cobicistat of the Compound of Formula-1

(S)—N-((2R,5R)-5-amino-1,6-diphenylhexan-2-yl)-2-(3-((2-isopropylthiazol-4-yl)methyl)-3-methylureido)-4-morpholinobutanamide (2 gm) was dissolved in isopropanol (10 ml). Diisopropyl ethylamine (0.54 gm), L-ascorbic acid (0.055 gm) and 4-nitrophenyl thiazol-5-ylmethyl carbonate (0.79 gm) were slowly added to the above reaction mixture at 25-30° C. and stirred it for 18 hrs at the same temperature. Water was added to the reaction mixture and stirred for 10 minutes at 25-30° C. Acidified the reaction mixture with dilute hydrochloric acid solution and dichloromethane was added to it. Separated both the organic and aqueous layers. Aqueous citric acid solution was added to the organic layer and stirred for 10 minutes. Separated both the organic and aqueous layers. The compound was extracted from organic layer using aqueous citric acid solution. Combined the aqueous layers, dichloromethane was added to the aqueous layer and neutralized the reaction mixture with saturated sodium carbonate solution at 10-15° C. Separated both the organic and aqueous layers. Aqueous layer was extracted with dichloromethane. Combined the organic layers and washed with aqueous sodium carbonate solution. Silicondioxide (3 gm) was added to the organic layer at 20-25° C. and stirred the reaction mixture for 30 minutes at the same temperature. Filtered the reaction mixture and washed with dichloromethane. The filtrate was acidified saturated citric acid solution and separated both the organic and aqueous layers. Aqueous layer was washed with dichloromethane at 10-15° C. Dichloromethane was added to aqueous layer at 10-15° C. and neutralized the reaction mixture using aqueous sodium carbonate solution and stirred for 20 minutes at the same temperature. Separated both the organic and aqueous layers and the aqueous layer was extracted with dichloromethane. Combined the organic layers, washed with water and distilled off the solvent from the organic layer completely to get the title compound. Yield: 1.2 gm Example-21

Preparation of Solid Dispersion of Cobicistat with Silicondioxide (S)—N-((2R,5R)-5-amino-1,6-diphenylhexan-2-yl)-2-(3-((2-isopropylthiazol-4-yl)methyl)-3-methylureido)-4-morpholinobutanamide (50 gm) was dissolved in isopropanol (200 ml) and cooled to 10-15° C. Diisopropyl ethylamine (10.2 gm), L-ascorbic acid (1.38 gm) and 4-nitrophenyl thiazol-5-ylmethyl carbonate (17.6 gm) were added to the above reaction mixture at 10-15° C. Raised the temperature of the reaction mixture to 25-30° C. and stirred it for 18 hrs at the same temperature. Water was added to the reaction mixture and stirred for 10 minutes at 25-30° C. Acidified the reaction mixture with dilute hydrochloric acid solution and dichloromethane was added to it. Separated both the organic and aqueous layers. Aqueous citric acid solution was added to the organic layer and stirred for 10 minutes. Separated both the organic and aqueous layers. The compound was extracted from organic layer using aqueous citric acid solution. Combined the aqueous layers, dichloromethane was added to the aqueous layer and neutralized the reaction mixture with saturated sodium carbonate solution at 10-15° C. Separated both the organic and aqueous layers. Organic layer was washed with 5% aqueous citric acid solution and followed by with 5% aqueous sodium carbonate solution. Cooled the organic layer to 10-15° C., silicondioxide (100 gm) was added to the organic layer at 10-15° C. and stirred the reaction mixture for 60 minutes at the same temperature. Filtered the reaction mixture and washed with dichloromethane. The filtrate was washed with 5% aqueous citric acid solution. Acidified the organic layer with saturated citric acid solution and separated both the organic and aqueous layers. Aqueous layer was washed with dichloromethane at 10-15° C. Dichloromethane was added to aqueous layer at 10-15° C. and neutralized the reaction mixture using aqueous sodium carbonate solution and stirred for 20 minutes at the same temperature. Separated both the organic and aqueous layers and the organic layer was cooled to 10-15° C. Filtered the organic layer through hyflow bed and washed with dichloromethane. Silicon dioxide (25 gm) was added to the filtrate at 5-10° C. and distilled off the solvent completely form the reaction mixture under reduced pressure. Co-distilled with n-hexane, 500 ml of n-hexane was added to the obtained compound at 25-30° C. and stirred the reaction mixture for 45 minutes. Filtered the obtained solid, washed with n-hexane and dried to get the title compound. Yield: 43 gm; HPLC purity: 99.75%, Chiral Purity: 99.25%, RRR Isomer impurity: 0.75%.

Particle size distribution: D10: 19.143 µm, D50: 43.301 µm, D90: 84.854 µm.

Figure 4:
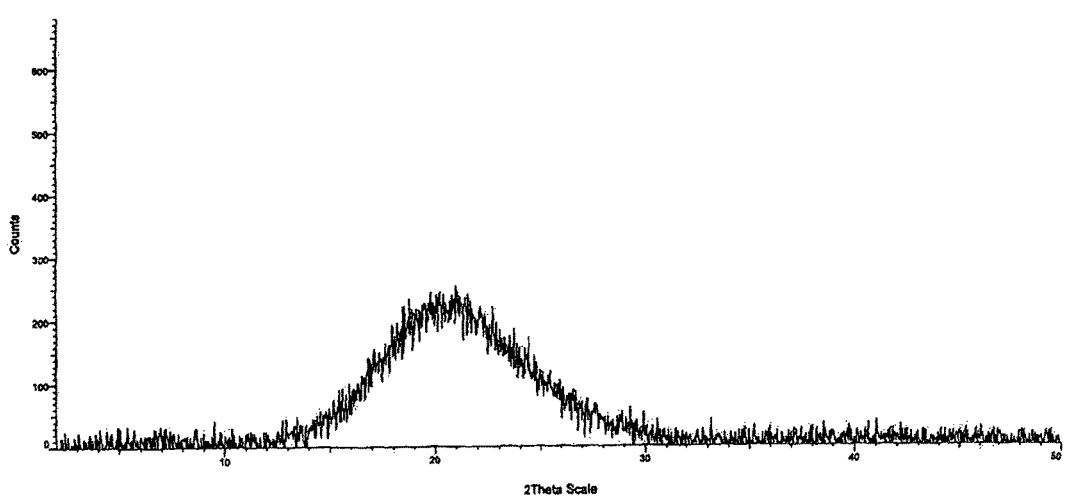
FIG. 4: Illustrates the PXRD pattern of solid dispersion of the compound of formula-1 with silicondioxide

PXRD of the obtained compound was illustrated in FIG. 4

Example-22

Preparation of (S)-ethyl-2-(3-((2-isopropylthiazol-4-yl)methyl)-3-methyl ureido)-4-morpholinobutanoate oxalate Compound of Formula-6b (R=$C_2H_5$, Acid=Oxalic Acid)

Sodium iodide (88.2 gm) was added to a mixture of (S)-1-((2-isopropylthiazol-4-yl)methyl)-1-methyl-3-(2-oxo-tetrahydrofuran-3-yl)urea (50 gm), ethanol (60 ml) and dichloromethane (250 ml) at 25-30° C. under nitrogen atmosphere. Cooled the reaction mixture to 10-15° C. and trimethyl silyl chloride (70.3 gm) was slowly added to the reaction mixture at 10-15° C. Raised the temperature of the reaction mixture to 20-25° C. and stirred for 6 hrs at the same temperature. Cooled the reaction mixture to 0-5° C. Morpholine (147 ml) was slowly added to the reaction mixture at 0-5° C. and temperature of the reaction mixture was raised to 20-25° C. Stirred the reaction mixture for 12 hrs at 20-25° C. Water and dichloromethane were added to the reaction mixture and stirred for 30 minutes. Both the organic and aqueous layers were separated. Water was added to the organic layer and adjusted the pH of the reaction mixture to 6.0 with oxalic acid. Both the organic and aqueous layers were separated and organic layer was dried with sodium sulphate. Distilled off the solvent completely from the organic layer under reduced pressure and co-distilled with acetone. Acetone (250 ml) was added to the obtained compound and stirred for 10 minutes at 25-30° C. A solution of Oxalic acid (30 gm) dissolved in acetone (200 ml) was added to the reaction mixture at 25-30° C. Heated the reaction mixture to 55-60° C. and stirred for 45 minutes at the same temperature. Cooled the reaction mixture to 25-30° C., further cooled to 0-5° C. and stirred the reaction mixture for 4 hrs at 0-5° C. The obtained solid was filtered, washed with acetone. The obtained compound was recrystallized using acetone and dried to get the title compound. Yield: 52.5 gm; M.R.: 142-145° C.

Example-23

Preparation of thiazol-5-ylmethyl (2R, 5R)-5-amino-1,6-diphenylhexan-2-yl)carbamate hydrochloride Basified the mixture of (2R, 5R)-1,6-diphenylhexane-2, 5-diamine dihydrochloride (100 gm) and dichloromethane (1300 ml) using aqueous sodium hydroxide solution at 5-10° C. Raised the temperature of the reaction mixture to 25-30° C. Both the organic and aqueous layers were separated and the organic layer was washed with water. Dichloromethane (1500 ml) and 4-nitrophenyl thiazol-5-ylmethyl carbonate (88.5 gm) were added to the organic layer at 25-30° C. Heated the reaction mixture to 40-45° C. and stirred for 18 hrs at the same temperature. Water was added to the reaction mixture and stirred for 20 minutes at 25-30° C. Both the organic and aqueous layers were separated. Organic layer was washed with aqueous sodium hydroxide solution and followed by water. Acidifying the reaction mixture with satureated citric acid solution and separated both the organic and aqueous layers. Aqueous layer was washed with dichloromethane and dichloromethane was added to the aqueous layer. Basified the reaction mixture with aqueous potassium carbonate solution. Separated both the organic and aqueous layers. The aqueous layer was extracted with dichloromethane and combined the organic layers. Distilled off the solvent completely from the organic layer under reduced pressure. Ethyl acetate (750 ml) was added to the obtained compound and ethylacetate-HCl (200 ml) was added to the reaction mixture at 20-25° C. Stirred the reaction mixture for 45 minutes at the same temperature. Filtered the obtained solid, washed with ethyl acetate and dried to get the title compound. Yield: 102.5 gm; M.R.: 202-205° C.

Example-24

Preparation of Solid Dispersion of Cobicistat with Silicondioxide

Water (185 ml) was added to a mixture of (S)-ethyl-2-(3-((2-isopropylthiazol-4-yl)methyl)-3-methylureido)-4-morpholinobutanoate oxalate (100 gm) and dichloromethane (550 ml) at 25-30° C. Cooled the reaction mixture to 10-15° C. Basified the reaction mixture with aqueous potassium bicarbonate solution. Both the organic and aqueous layers were separated and the organic layers and washed with water. Distilled off the solvent completely from the organic layer under reduced pressure. Dichloromethane (100 ml) was added the above obtained compound at 25-30° C. and cooled the reaction mixture to 5-10° C. A solution of potassium hydroxide (27 gm) in 60 ml of water was slowly added to the reaction mixture at 5-10° C. and stirred for 15 hrs at the same temperature. Dichloromethane (600 ml) was added to the reaction mixture at 5-10° C. and cooled to −25 to −20° C. Thiazol-5-ylmethyl (2R, 5R)-5-amino-1,6-diphenylhexan-2-yl)carbamate hydrochloride (67 gm) was added to the reaction mixture at −25 to −20° C. and stirred for 60 minutes at the same temperature. HOBT (32 gm) was added to the above reaction mixture at −25 to −20° C. and stirred for 60 minutes at the same temperature. A solution of EDC.HCl (60 gm) in 600 ml of dichloromethane was slowly added to the above reaction mixture at −25 to −20° C. and stirred for 33 hrs at the same temperature. Raised the temperature of the reaction mixture to 0-5° C. and quenched the reaction mixture using 10% aqueous citric acid solution and stirred for 30 minutes at the same temperature. Both the organic and aqueous layers were separated and the organic layer was washed with 10% aqueous citric acid solution. Organic layer was washed with 20% aqueous potassium carbonate solution and followed by water. The compound was extracted into saturated citric acid solution from the organic layer at 0-5° C. The aqueous layer was washed with dichloromethane and dichloromethane was added to the aqueous layer at 5-10°. Neutralized the reaction mixture using aqueous potassium carbonate solution. Separated both the organic and aqueous layers and aqueous layer was extracted with dichloromethane. Combined the organic layers and carbon (15.4 gm) was added to it at 20-25° C. Stirred the reaction mixture for 30 minutes at 20-25° C., filtered the reaction mixture on hyflow bed and washed with dichloromethane. Distilled off the solvent completely from the filtrate under reduced pressure. Dichloromethane (300 ml) and n-heptane (335 ml) were added to the obtained compound at 20-25° C. and stirred for 25 minutes. Silicondioxide (113.8 gm) was added to the reaction mixture in lot wise over a period of 1 hr at 20-25° and stirred the reaction mixture for 3 hrs at the same temperature. n-Heptane (846 ml) was slowly added to the reaction mixture at 20-25° C. and stirred for 3 hrs at the same temperature. Distilled off the solvent upto 6 volumes from the reaction mixture under reduced pressure. Cooled the reaction mixture to 20-25° C. and filtered the obtained solid. Washed the solid with n-heptane and dried to get the title compound. Yield: 180 gm Example-25

Preparation of (S)-2-(tert-butoxycarbonylamino)-3-phenylpropanoic acid [Formula-31a, P1=H, P2=BOC]

Aqueous Sodium bicarbonate solution was added to a mixture of L-phenyl alanine (20 gms) and 1,4-dioxane (100 ml) at 25-30° C. and stirred for 10 minutes at the same temperature. Di-tertiary-butyl dicarbonate [DIBOC] (29 gm) was slowly added to the reaction mixture at 0-5° C. Raised the temperature of the reaction mixture to 25-30° C. and stirred for 3 hours at the same temperature. Distilled off the solvent from the reaction mixture under reduced pressure. Ethyl acetate was added to the reaction mixture at 25-30° C. and stirred for 10 minutes at the same temperature. Both the organic and aqueous layers were separated and aqueous layer was acidified using 5% hydrochloric acid. Ethyl acetate was added to the aqueous layer at 25-30° C. and stirred for 20 minutes at the same temperature. Both the organic and aqueous layers were separated and aqueous layer was extracted with ethyl acetate. Combined the organic layers and distilled off the solvent completely from the organic layer under reduced pressure to get the title compound. Yield: 31 gms Example-26

Preparation of (S)-tert-butyl 1-hydroxy-3-phenylpropan-2-ylcarbamate [Formula-32a; P1=H, P2=BOC]

Sodium borohydride was added slowly to a mixture of (S)-2-(tert-butoxycarbonylamino)-3-phenylpropanoic acid (5 gms) and tetrahydrofuran (40 ml) at 0-5° C. Boron trifluoride diethyl etherate was slowly added to the reaction mixture at 0-5° C. Raised the temperature of the reaction mixture to 25-30° C. and stirred for 4½ hours at the same temperature. Cooled the reaction mixture to 0-5° C. and water was slowly added to it at the same temperature. Ethyl acetate was added to the reaction mixture at 25-30° C. and stirred for 20 minutes at the same temperature. Both the organic and aqueous layers were separated and the aqueous layer was extracted with ethyl acetate. Combined the organic layers and distilled off the solvent completely from the organic layer under reduced pressure to get the title compound. Yield: 3 gms Example-27

Preparation of (S)-tert-butyl 1-oxo-3-phenylpropan-2-ylcarbamate

A mixture of (S)-tert-butyl 1-hydroxy-3-phenylpropan-2-ylcarbamate (5 gm) and dichloromethane (50 ml) was slowly added to a solution of Dess-martin periodinone (9.28 gms) in dichloromethane (45 ml) at 10-15° C. Raised the temperature of the reaction mixture to 25-30° C. and stirred for 3 hours at the same temperature. Sodium thiosulfate and aqueous sodium bicarbonate solution were added to the reaction mixture at 25-30° C. and stirred for 45 minutes at the same temperature. Dichloromethane was added to the reaction mixture at 25-30° C. and stirred for 30 minutes at the same temperature. Both the organic and aqueous layers were separated and aqueous layer was extracted with dichloromethane. Combined the organic layers and washed with aqueous sodium bicarbonate solution. Distilled off the solvent completely from the organic layer to get the title compound.

Yield: 6 gms.

Example-28

Preparation of thiazol-5-ylmethyl 1H-imidazole-1-carboxylate

Carbonyl diimidazole [CDI] (70 gms) was slowly added to a mixture of thiazol-5-ylmethanol (50 gms) and dichloromethane (400 ml) at 10-15° C. and stirred for 10 minutes at the same temperature. Triethyl amine was slowly added to the reaction mixture at 10-15° C. and stirred for 3 hours at the same temperature. Filtered the solid and washed with dichloromethane. Water was added to the obtained wet compound at 25-30° C. and stirred for 3 hours at the same temperature. Filtered the solid, washed with water and dried to get the title compound. Yield: 38 gms.

Example-29

Preparation of Solid Dispersion of Cobicistat with Silicon Dioxide

Triethylamine (10.97 ml) was added to a mixture of (S)—N-((2R,5R)-5-amino-1,6-diphenylhexan-2-yl)-2-(3-((2-isopropylthiazol-4-yl)methyl)-3-methylureido)-4-morpholino butanamide (25 gm) and dichloromethane (125 ml) at 25-30° C. Heated the reaction mixture to 40-43° C. and stirred for 10 minutes at the same temperature. Thiazol-5-ylmethyl 1H-imidazole-1-carboxylate in dichloromethane was slowly added to the reaction mixture at 40-43° C. and stirred for 7 hours at the same temperature. Distilled off the solvent completely from the reaction mixture. Dichloromethane (25 ml) was added to the reaction mixture at 35-40° C. and stirred for 8 hours at the same temperature. Another lot of Thiazol-5-ylmethyl 1H-imidazole-1-carboxylate in dichloromethane was added to the reaction mixture at 35-40° C. and stirred for 7 hours at the same temperature. The reaction mixture pH was adjusted to 4-5 using 5% citric acid solution. Water and dichloromethane were added to the reaction mixture at 15-20° C. and stirred for 30 minutes at the same temperature. Both the organic and aqueous layers were separated and organic layer was washed with 5% aqueous citric acid solution. 50% aqueous citric acid solution was added to the organic layer at 15-20° C. and stirred for 30 minutes at the same temperature. Both the organic and aqueous layers were separated and aqueous layer was washed with dichloromethane. Dichloromethane was added to the aqueous layer and cooled to 10-15° C. Reaction mixture was basified using 20% aqueous potassium carbonate solution. Both the organic and aqueous layers were separated and the aqueous layer was extracted with dichloromethane. Combined the organic layers and carbon was added to it and stirred for 30 minutes at 25-30° C. Filtered the reaction mixture through hyflow bed and washed with dichloromethane. Distilled off the solvent completely from the filtrate. Dichloromethane (75 ml) and n-heptane (125 ml) were added to the reaction mixture at 25-30° C. and stirred for 1 hour at the same temperature. Silicondioxide (18 gm) was slowly added lot-wise to the reaction mixture at 25-30° C. and stirred for 1 hour at the same temperature. n-heptane (200 ml) was slowly added to the reaction mixture at 25-30° C. Distilled off the solvent reached upto 150 ml of the solvent from the reaction mixture at 35° C. Filtered the solid, washed with n-heptane and dried to get the title compound. Yield: 27 gms.

Example-30

Preparation of Solid Dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl) butanoyl]amino}-1,6-diphenylhexan-2-yl]carbamate (Formula-1) in Combination with MCC (in the Ratio of 1:1)

Dichloromethane (10 ml) was added to 1,3-thiazol-5-ylmethyl [(2R,5R)-5-{[(2S)2-[(methyl {[2-(propan-2-yl)-1,3-thiazol-4-yl]methyl}carbamoyl)amino]-4-(morpholin-4yl) butanoyl] amino}-1,6-diphenylhexan-2-yl]carbamate (0.5 gms) at 25-30° C. Micro crystalline cellulose (0.5 gms) was added to the reaction mixture at 25-30° C. and stirred for 30 minutes at the same temperature. Distilled off the solvent completely from the reaction mixture to get the title compound. Yield: 0.65 gms. The PXRD pattern of the obtained compound was depicted in FIG. 1.

Example-31

Preparation of Solid Dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl)butanoyl]amino}-1,6-diphenylhexan-2-yl]carbamate (Formula-1) in Combination with MCC (in the Ratio of 1:1.5)

Dichloromethane (10 ml) was added to 1,3-thiazol-5-ylmethyl [(2R,5R)-5-{[(2S)2-[(methyl {[2-(propan-2-yl)-1,3-thiazol-4-yl]methyl}carbamoyl)amino]-4-(morpholin-4yl) butanoyl]amino}-1,6-diphenylhexan-2-yl]carbamate (0.5 gms) at 25-30° C. Micro crystalline cellulose (0.75 gms) was added to the reaction mixture at 25-30° C. and stirred for 30 minutes at the same temperature. Distilled off the solvent completely from the reaction mixture to get the title compound. Yield: 1.9 gms.

Example-32

Preparation of Solid Dispersion of 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl) butanoyl]amino}-1,6-diphenylhexan-2-yl]carbamate (Formula-1) in Combination with MCC (in the Ratio of 1:2.3)

Dichloromethane (10 ml) was added to 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl) butanoyl]amino}-1,6-diphenylhexan-2-yl]carbamate (0.3 gms) at 25-30° C. Micro crystalline cellulose (0.7 gms) was added to the reaction mixture at 25-30° C. and stirred for 30 minutes at the same temperature. Distilled off the solvent completely from the reaction mixture to get the title compound.

Figure 2:
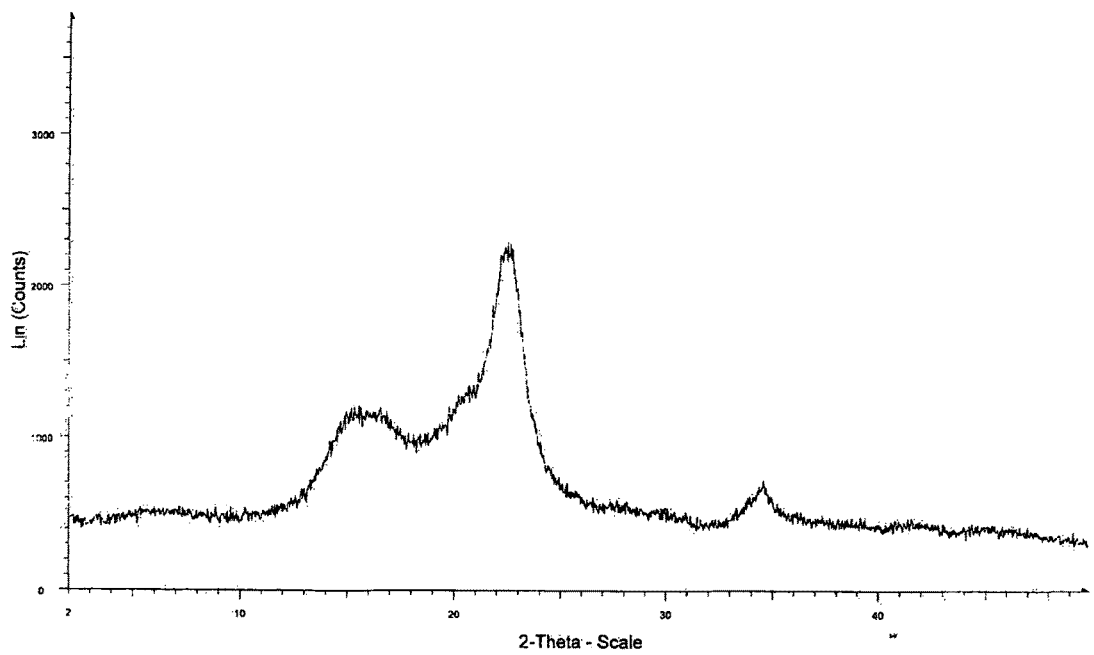
FIG. 2: Illustrates the PXRD pattern of solid dispersion of the compound of formula-1 with MCC in the ratio of 1:2.3.

Yield: 0.6 gms. The PXRD pattern of the obtained compound was depicted in FIG. 2.

Example-33

Preparation of Solid Dispersion of 1,3-thiazol-5-ylmethyl [(2R,5R)-5-{[(2S)2-[(methyl {[2-(propan-2-yl)-1,3-thiazol-4-yl]methyl}carbamoyl)amino]-4-(morpholin-4yl) butanoyl]amino}-1,6-diphenylhexan-2-yl]carbamate (Formula-1) in Combination with HPMC (in the Ratio of 1:1)

Dichloromethane (10 ml) was added to 1,3-thiazol-5-ylmethyl [(2R,5R)-5-{[(2S)2-[(methyl{[2-(propan-2-yl)-1,3-thiazol-4-yl]methyl}carbamoyl)amino]-4-(morpholin-4yl) butanoyl]amino}-1,6-diphenylhexan-2-yl]carbamate (0.5 gms) at 25-30° C. and stirred for 20 minutes at the same temperature. Hydroxypropyl methyl cellulose (0.5 gms) was added to the reaction mixture at 25-30° C. and stirred for 30 minutes at the same temperature. Distilled off the solvent completely from the reaction mixture to get the title compound. Yield: 0.6 gms.

Figure 3:
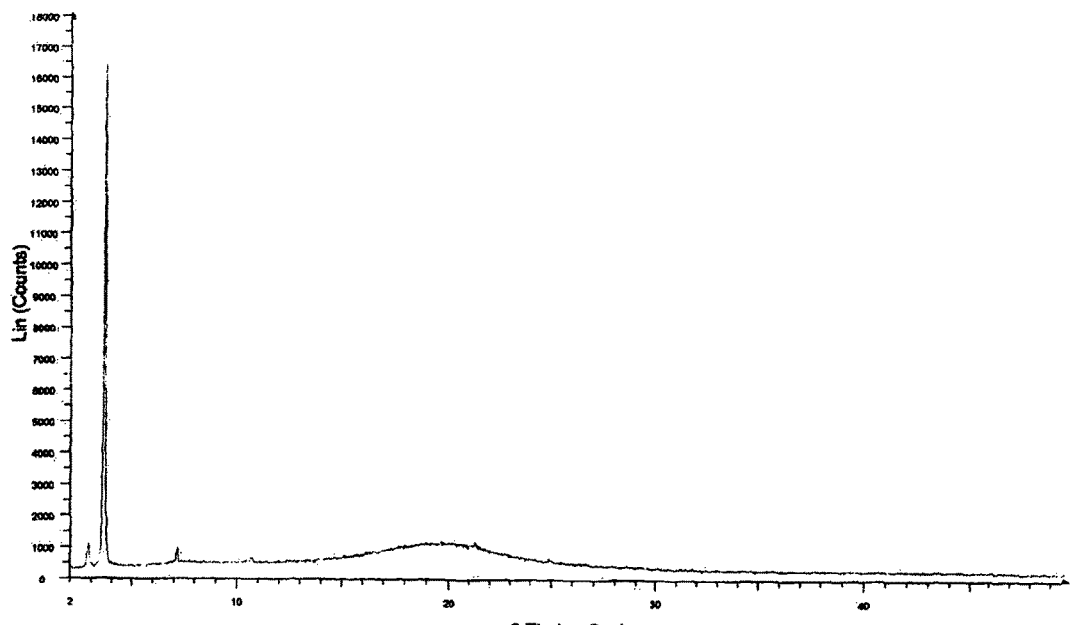
FIG. 3: Illustrates the PXRD pattern of solid dispersion of the compound of formula-1 with HPMC in the ratio of 1:1.

The PXRD pattern of the obtained compound was depicted in FIG. 3.

We claim:

1. A process for the preparation of 1,3-thiazol-5-ylmethyl [(2R,5R)-5-{[(2S)-2-[(methyl{[2-(propan-2-yl)-1,3-thiazol-4-yl]methyl} carbamoyl)amino]-4-(morpholin-4-yl) butanoyl]amino}-1,6-diphenylhexan-2-yl]carbamate compound of formula-1

Formula-1

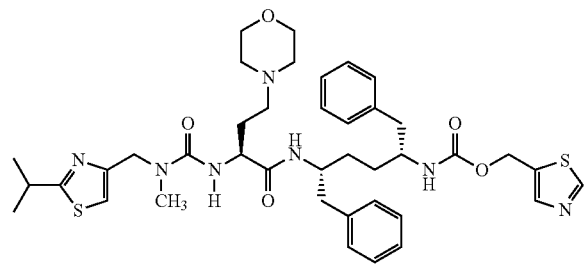

comprising:
a) reacting the compound of formula-10

Formula-10

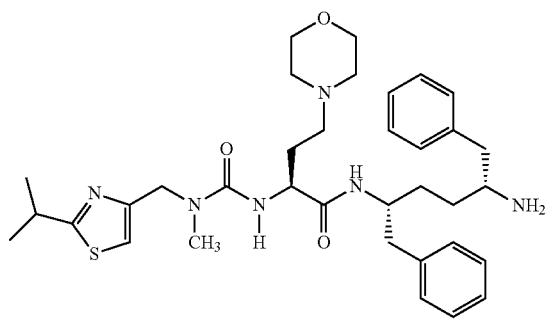

with the compound of general formula-13

Formula-13

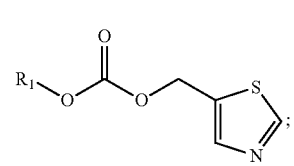

wherein $R_1$ is selected from the group consisting of straight or branched chain alkyl, aralkyl, aryl, and substituted aralkyl/aryl group;
in presence of a base in a solvent in presence or absence of antioxidant to obtain the compound of formula-1, and
b) optionally purifying the compound of formula-1 from the solvent to provide pure compound of formula-1;
wherein the base in step a) is selected from inorganic bases and organic bases; the antioxidant is selected from thiols and ascorbic acid; the solvent in step a) and step b) is selected from the group consisting of alcohol solvents, ether solvents, nitrile solvents, chloro solvents, ester solvents, polar aprotic solvents, ketone solvents, hydrocarbon solvents and polar solvents or mixture thereof.

2. The process according to claim 1, wherein the compound of general formula-13 in step a) is formula-13a:

Formula-13a

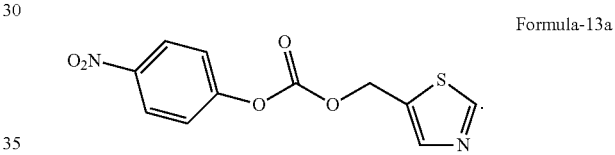

3. The process according to claim 1; further comprising:
a) dissolving the compound of formula-1 obtained according to claim 1 in a solvent,
b) adding silicon dioxide to the mixture obtained in step a),
c) distilling off the solvent from the mixture,
d) adding a second solvent to obtained compound in step c), and
e) isolating solid dispersion of the compound of formula-1 with silicon dioxide
wherein suitable solvent in step a) is selected from chloro solvents, hydrocarbon solvents or mixtures thereof; suitable solvent in step d) is selected from hydrocarbon solvent.

4. The process according to claim 3, comprising:
a) dissolving compound of formula-1 in dichloromethane,
b) adding silicon dioxide to the mixture obtained in step a),
c) distilling off the solvent from the mixture,
d) adding n-hexane to the obtained compound in step c), and
e) filtering the obtained solid in step d) to provide solid dispersion of compound of formula-1 with silicondioxide.

5. The process according to claim 4, wherein the compound of formula-1 with silicon dioxide is obtained as amorphous compound.

6. An amorphous compound of formula-1 according to claim 5 having purity >99%.

7. An amorphous compound of formula-1 according to claim 5 having chiral purity >99%.

8. The process according to claim 1, wherein the base in step a) is diisopropyl ethylamine.

9. The process according to claim 1, wherein the solvent in step a) is isopropanol.

10. The process according to claim 1, wherein antioxidant in step a) is L-ascorbic acid.

11. The process of claim 1, further comprising a process for the preparation of the compound of formula-10; wherein the process for the preparation of the compound of formula-10 comprises:

a) reacting the compound of general formula-5 or general formula-6

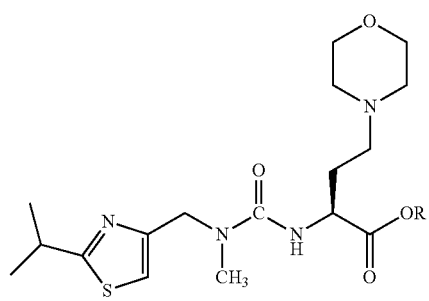

Formula-5

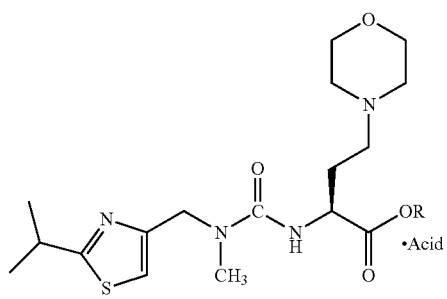

Formula-6 wherein
R is selected from the group consisting of straight or branched chain alkyl, aralkyl, aryl, and substituted aralkyl/aryl group;
with a base in a solvent to provide compound of general formula-7,

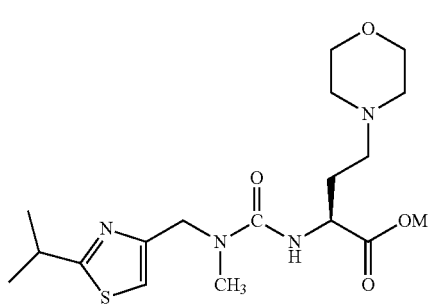

Formula-7 wherein M is selected from the group consisting of Li, Na, K and H;

b) reacting the compound of general formula-7 in-situ with the compound of general formula-8 or its salts

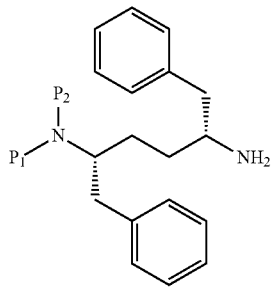

Formula-8 wherein $P_1$, $P_2$ are independently selected from H or amine protecting group with the proviso that $P_1$ and $P_2$ both are not 'H';

in presence of a coupling agent in a solvent to provide the compound of general formula-9

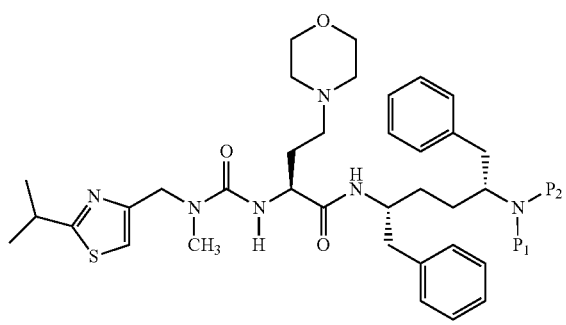

Formula-9 wherein $P_1$, $P_2$ are as defined above, and c) treating the compound of general formula-9 with a deprotecting agent in a solvent to provide compound of formula-10.

12. The process according to claim 11, wherein the base in step a) is an inorganic base;

the coupling agent in step b) is selected from the group consisting of DCC, CDI, DIC, EDC.HCl, and the like; optionally in combination with HOAt, HOBt, HOCt, TBTU, DMAP optionally in presence of a base;

the deprotecting agent in step c) is selected from an acid; and the solvent in step a), step b) and step c) is selected from the group consisting of alcohol solvents, ether solvents, nitrile solvents, chloro solvents, ester solvents, polar aprotic solvents, ketone solvents, hydrocarbon solvents and polar solvents or mixture thereof.

13. The process according to claim 11, wherein the base in step a) is potassium hydroxide, the solvent is a mixture of dichloromethane and water; the compound of general formula-5 is formula-5a; the compound of general formula-6 is formula-6a; and the compound of general formula-7 is formula-7a:

Formula-5a

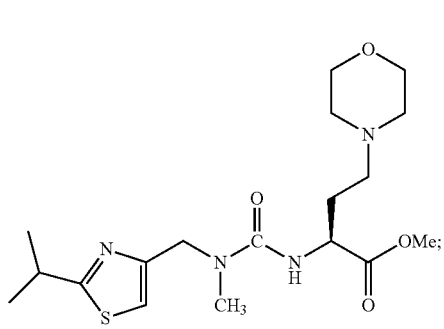

Formula-6a

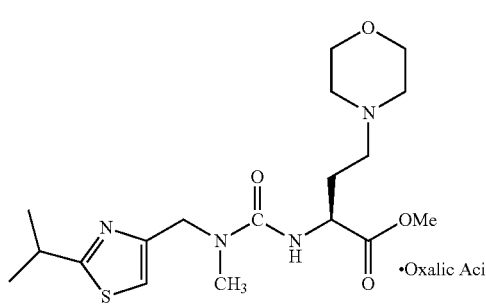

Formula-7a

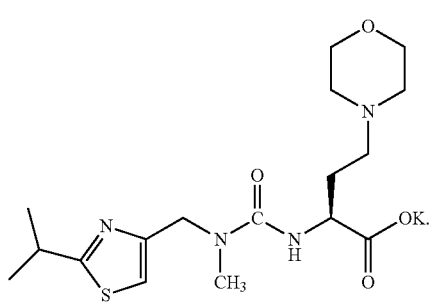

14. The process according to claim 11, wherein the coupling agent in step b) is selected from the group consisting of EDC.HCl, HOBT and di isopropyl ethyl amine; the compound of general formula-8 is formula-8a$_1$ and the compound of general formula-9 is formula-9a:

Formula-8a$_1$

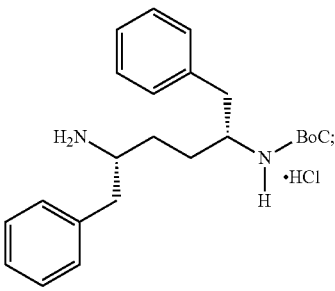

Formula-9a

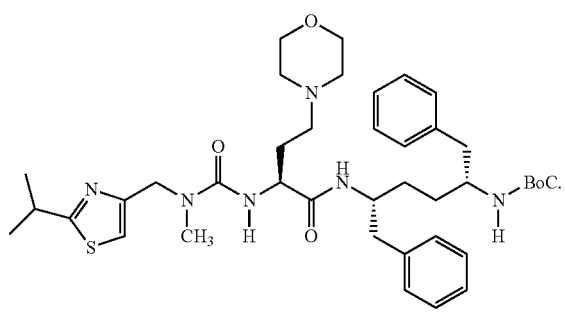

15. The process according to claim 11, wherein the deprotecting agent in step c) is hydrochloric acid, and the solvent is dichloromethane.

16. The process of claim 14, further comprising a process for the preparation of the compound of formula-8a$_1$; wherein the process for the preparation of the compound of formula-8a$_1$ comprises:

a) treating (2R, 5R)-5-amino-1,6-diphenylhexan-2-yl-carbamate dihydrochloride with DIBOC in presence of triethylamine in methanol to obtain tert-butyl (2R, 5R)-5-amino-1,6-diphenylhexan-2-yl-carbamate, b) treating tert-butyl (2R, 5R)-5-amino-1,6-diphenylhexan-2-yl-carbamate obtained in step a) with ethyl acetate HCl in ethyl acetate, and c) purifying the compound obtained in step b) in the mixture of ethyl acetate and water to obtain the compound of formula-8a$_1$.

* * * * *